(12) United States Patent
Parker et al.

(10) Patent No.: US 8,696,558 B1
(45) Date of Patent: *Apr. 15, 2014

(54) PEDICLE GUIDED RETRACTOR SYSTEM

(75) Inventors: Jared Parker, Denver, CO (US); Jeffery Thramann, Longmont, CO (US); Michael Fulton, Superior, CO (US); Jeffrey Henn, Ft. Myers, FL (US); Saman P. Javedan, Ft. Myers, FL (US)

(73) Assignee: Lanx, Inc., Broomfield, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/593,177

(22) Filed: Aug. 23, 2012

Related U.S. Application Data

(63) Continuation of application No. 12/630,564, filed on Dec. 3, 2009, now Pat. No. 8,251,902, which is a continuation-in-part of application No. 11/251,689, filed on Oct. 17, 2005, now abandoned.

(60) Provisional application No. 61/200,959, filed on Dec. 5, 2008.

(51) Int. Cl.
  *A61B 1/32* (2006.01)
(52) U.S. Cl.
  USPC .......................................................... 600/215
(58) Field of Classification Search
  USPC .................................................. 600/201–246
  See application file for complete search history.

(56) References Cited

U.S. PATENT DOCUMENTS

| | | | |
|---|---|---|---|
| 5,728,046 A | 3/1998 | Mayer et al. | |
| 5,885,293 A | 3/1999 | McDevitt | |
| 5,961,522 A | 10/1999 | Mehdizadeh | |
| 7,014,608 B2 | 3/2006 | Larson et al. | |
| 7,156,805 B2 | 1/2007 | Thalgott et al. | |
| 7,182,729 B2 | 2/2007 | Abdelgany et al. | |
| 7,207,949 B2 | 4/2007 | Miles et al. | |
| 7,435,219 B2 | 10/2008 | Kim | |
| 2002/0013514 A1 | 1/2002 | Brau | |
| 2003/0199874 A1 | 10/2003 | Michelson | |
| 2004/0116777 A1 | 6/2004 | Larson et al. | |
| 2004/0220567 A1 | 11/2004 | Eisermann et al. | |
| 2004/0243130 A1 | 12/2004 | Biscup | |
| 2005/0080320 A1 | 4/2005 | Lee et al. | |
| 2005/0080418 A1 | 4/2005 | Simonson et al. | |
| 2005/0090822 A1 | 4/2005 | DiPoto | |
| 2005/0137461 A1 | 6/2005 | Marchek et al. | |

(Continued)

OTHER PUBLICATIONS

Zimmer ARAS Retractor Instrumentation pamphlet for Zimmer Spine, 2007, www.zimmerspine.com, 19 pages.

*Primary Examiner* — Sameh Boles
(74) *Attorney, Agent, or Firm* — Perkins Coie LLP

(57) ABSTRACT

There is disclosed a retractor system to facilitate surgical access to an intervertebral disc between an inferior vertebral body and a superior vertebral body. In an embodiment, the retractor system includes an elongate member having an anchor to attach to a pedicle of an inferior vertebral body with respect to an intervertebral disc. A retractor body has a collar to attach to the elongate member, slides coupled to the retractor body, and a pair of blades mounted to the slides. The blades have a proximal end and a distal end, a distance between the proximal end and the distal end of each one of the blades configured for displacing tissue for access to an intervertebral disc. An attachment portion is adjacent the proximal end of each one of the blades for attaching one of the slides thereto. Geometry of the blade end conforms to anatomy surrounding the pedicle.

18 Claims, 45 Drawing Sheets

(56) References Cited

U.S. PATENT DOCUMENTS

| | | |
|---|---|---|
| 2005/0149035 A1 | 7/2005 | Pimenta et al. |
| 2005/0159650 A1 | 7/2005 | Raymond et al. |
| 2005/0159651 A1 | 7/2005 | Raymond et al. |
| 2005/0192575 A1 | 9/2005 | Pacheco |
| 2005/0215862 A1 | 9/2005 | Larson et al. |
| 2005/0215866 A1 | 9/2005 | Kim |
| 2005/0273114 A1 | 12/2005 | Novak |
| 2005/0273167 A1 | 12/2005 | Triplett et al. |
| 2006/0025863 A1 | 2/2006 | Lamprich et al. |
| 2006/0052672 A1 | 3/2006 | Landry et al. |
| 2006/0069315 A1 | 3/2006 | Miles et al. |
| 2006/0074445 A1 | 4/2006 | Gerber et al. |
| 2006/0106415 A1 | 5/2006 | Gabbay |
| 2006/0149273 A1 | 7/2006 | Ross et al. |
| 2006/0155170 A1 | 7/2006 | Hanson et al. |
| 2006/0195107 A1 | 8/2006 | Jones et al. |
| 2006/0224044 A1 | 10/2006 | Marchek et al. |
| 2006/0224045 A1 | 10/2006 | Whipple et al. |
| 2006/0235338 A1 | 10/2006 | Pacheco |
| 2007/0021656 A1 | 1/2007 | Martin et al. |
| 2007/0038033 A1 | 2/2007 | Jones et al. |
| 2007/0100212 A1 | 5/2007 | Pimenta et al. |
| 2007/0123753 A1 | 5/2007 | Abdelgany et al. |
| 2007/0156024 A1 | 7/2007 | Frasier et al. |
| 2007/0156025 A1 | 7/2007 | Marchek et al. |
| 2007/0156026 A1 | 7/2007 | Frasier et al. |
| 2007/0198062 A1 | 8/2007 | Miles et al. |
| 2007/0208227 A1 | 9/2007 | Smith et al. |
| 2007/0208228 A1 | 9/2007 | Pavento et al. |
| 2007/0276191 A1 | 11/2007 | Selover et al. |
| 2007/0282171 A1 | 12/2007 | Karpowicz et al. |
| 2008/0021284 A1 | 1/2008 | Hestad et al. |
| 2008/0021285 A1* | 1/2008 | Drzyzga et al. ............... 600/215 |
| 2008/0058606 A1 | 3/2008 | Miles et al. |
| 2008/0097164 A1 | 4/2008 | Miles et al. |
| 2008/0132766 A1 | 6/2008 | Dant et al. |
| 2008/0214898 A1 | 9/2008 | Warren |
| 2008/0300465 A1 | 12/2008 | Feigenwinter et al. |

* cited by examiner

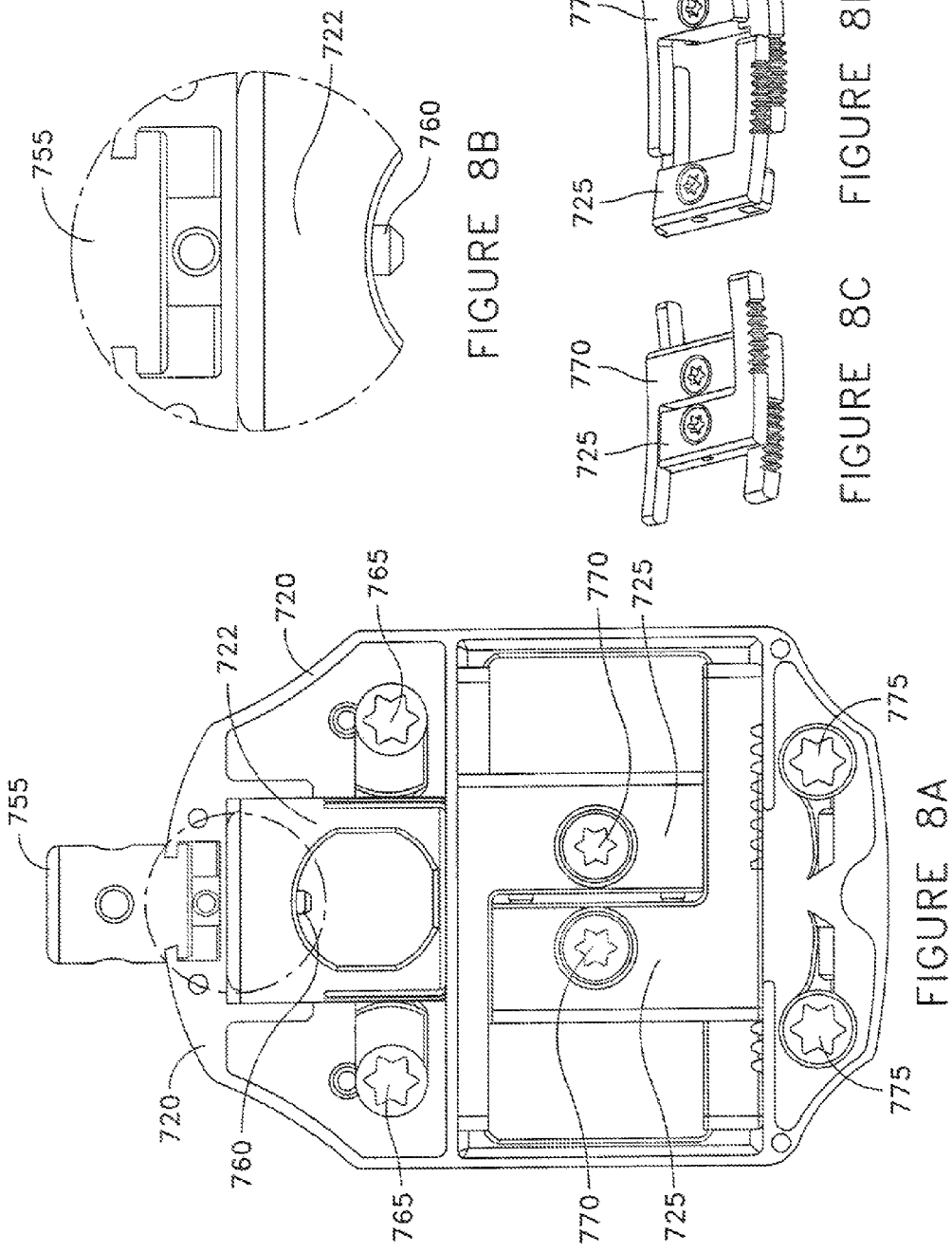

PEDICLE GUIDED RETRACTOR SYSTEM

REFERENCE TO PENDING PRIOR PATENT APPLICATIONS

This application is a continuation of U.S. patent application Ser. No. 12/630,564, titled Pedicle Guided Retractor System, filed Dec. 3, 2009, now U.S. Pat. No. 8,251,902, which is a continuation-in-part of pending prior U.S. patent application Ser. No. 11/251,689, filed Oct. 17, 2005, for Surgical Tools and Method to Facilitate Spinal Surgery, which claims the benefit of U.S. Provisional Patent Application No. 61/200,959, filed Dec. 5, 2008, for Pedicle Guided Retractor System.

The above-identified patent applications are hereby incorporated herein by reference.

BACKGROUND

The present disclosure relates to surgical tools and methods and, more particularly, to surgical tools and methods to facilitate spinal surgeries.

The spine can have many problems that require a surgeon to access locations around the vertebrae, including the intervertebral disc or disc space.

For example, in some instances, a surgeon may need to implant a graft to facilitate fusing adjacent vertebral bodies, such as, for example, during a transforaminal lumbar interbody fusion (TLIF) procedure. To implant the graft, the surgeon needs access to the vertebral disc to remove all or part of the disc nucleus and, in some cases, the disc annulus (generically referred to as "disc material"). After removal of the disc material, the surgeon implants a graft to facilitate fusion between the superior and inferior disc. Alternatively, a surgeon may implant an artificial disc instead of fusing the vertebral bodies. Frequently, to provide adequate access, the surgeon removes a portion of the bone associated with the vertebral column, such as, for example, a portion of the lamina, facet, or the like. Other locations that may need to be accessed include the facet joints, lamina, spinous processes, transverse processes, and other locations adjacent the spine.

As can be appreciated, the surgical site is relatively small for the procedure. Furthermore, the spinal cord and other nerves are located relatively close to the surgical area. To safely perform spine surgery, a surgeon, for example, may take a significant portion of the surgical time locating the various nerves and orienting them in the surgical area and referencing anatomical landmarks.

Thus, it would be desirous to develop a surgical tool and method that facilitates spinal surgical procedures.

SUMMARY

The present disclosure provides systems and methods to facilitate surgical access to a spinal surgical site, e.g., a vertebral disc. The method may begin, for example, by locating an inferior pedicle and guiding a bone cutting device relative to the inferior pedicle. The bone cutting device is used to remove a portion of the vertebral body to provide access to the disc space. Typically, the bone cutting device is removed and a speculum is inserted until the speculum approaches and/or pierces a disc annulus between the inferior vertebral body and a superior vertebral body. The speculum is moved to ensure the nerves are out of the surgical area. The speculum also provides a shield to inhibit inadvertent damage to the nerve while the surgeon is operating.

The present disclosure also provides systems to facilitate spinal surgery. One such system may comprise, for example, a bone cutter and a guide coupled to the bone cutter. The guide facilitates placement of the bone cutter on a portion of the inferior vertebral body to be removed to provide surgical access. The system may further include a speculum that is coupled to the guide. The speculum may have a surface proximate an annulus of the intervertebral disc. The surface may be movable to distract the nerve from the surgical access site, such that the system facilitates removal of bone and isolation of nerves to provide surgical access and reduce time in surgery.

Moreover, the present disclosure provides a tool to facilitate the removal of bone. The bone removal tool facilitates the surgical procedures. The bone removal tool may include a bone cutter and a bone cutter guide. The bone cutter guide may couple to or is integrated with the bone cutter. A track may be coupled to the bone cutter such that the bone cutter is movable on extenders to contact the bone.

There is disclosed retractor systems and methods to facilitate surgical access to the intervertebral disc space between adjacent vertebral bodies. In an embodiment, a retractor system includes an elongate member having an anchor to attach to an inferior vertebral body with respect to an intervertebral disc. A retractor body has an attachment device to attach to the elongate member, one or more slides coupled to the retractor body, and a pair of blades mounted to the slides. The blades have a proximal end and a distal end, with a distance between the proximal end and the distal end of each one of the blades configured for displacing tissue for access to an intervertebral disc. An attachment portion is adjacent the proximal end of each one of the blades for attaching one of the slides thereto. Geometry of the blade end conforms to anatomy surrounding the pedicle.

The foregoing and other features, utilities and advantages of the embodiments of the disclosure will be apparent from the following, more particular, description of a preferred embodiment as illustrated in the accompanying drawings.

BRIEF DESCRIPTION OF THE DRAWINGS

The accompanying drawings, which are incorporated in and constitute a part of this specification, illustrate embodiments of the present disclosure, and together with the description, serve to explain the principles thereof. Like items in the drawings are referred to using the same numerical reference.

FIG. 8A is a proximal plan view of the retractor system of FIG. 7 with the cover removed;

FIG. 8B is an enlarged view of a portion of FIG. 5A;

FIG. 8C is a view of the slides of FIG. 8 in a substantially closed position;

FIG. 8D is a view of the slides of FIG. 8 in a substantially opened position;

DETAILED DESCRIPTION

The technology of the present application will now be described with reference to the figures. The drawings are provided for illustration and should not be considered limiting or to scale. Moreover, although the technology of the present application is explained with specific reference to a TLIF procedure, one of ordinary skill in the art will recognize on reading the disclosure that the technology of the present application may be used in other surgical procedures, such as, for example, a posterior lumbar interbody fusion (PLIF) procedure, other fusion procedures, or the like. Moreover, while the examples provided for illustration relate to spinal surgery, one of ordinary skill in the art would recognize on reading the disclosure that the technology may be used in other procedures, such as, for example, laparoscopic procedures or the like.

Figure 1:
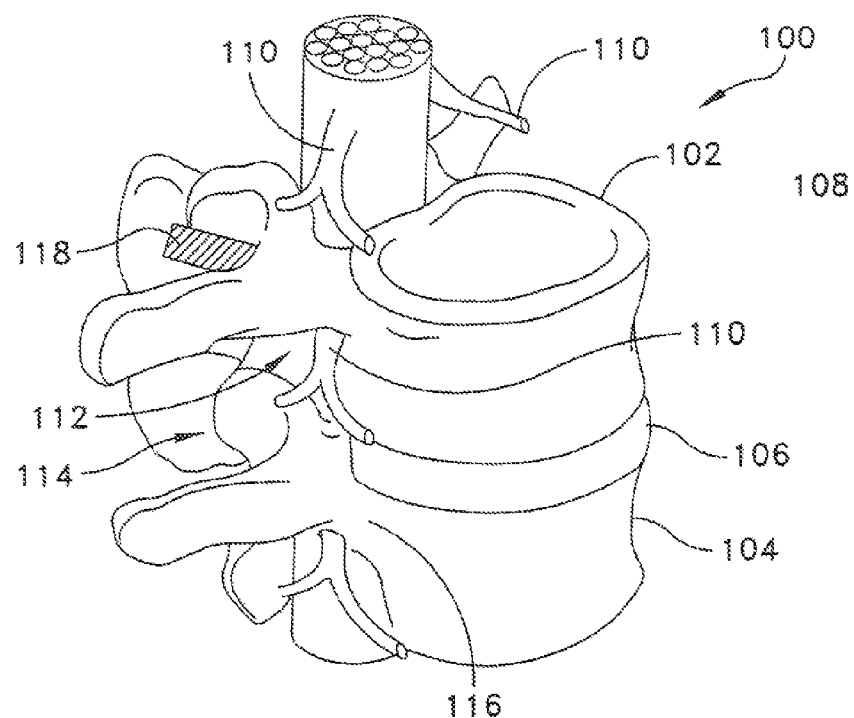
FIG. 1 is an anterior, lateral perspective view of a spinal segment.

FIG. 1 shows an anterior, lateral perspective view of a spinal segment 100. Spinal segment 100 includes superior vertebrae 102, inferior vertebrae 104, and an intervertebral disc 106. A spinal cord 108 has a number of nerves 110 extending from the spinal cord 108. As can be seen, the nerves 110 generally extend through the neural foramen 112 close to a pedicle of superior vertebrae 102.

Figure 2:
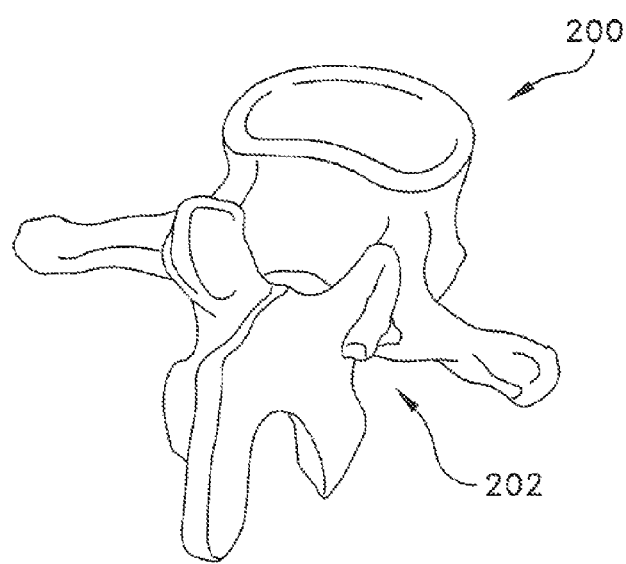
FIG. 2 is a posterior, lateral perspective view of a vertebra.

In a TLIF procedure, for example, often the surgeon removes a portion of the inferior vertebrae 104, such as, for example, the lamina or the facet, to allow surgical access to the intervertebral disc 106. FIG. 2 shows another view of the spinal segment 100 with a view of the lamina 202 and the facet 114.

In the TLIF procedure, a rod may be coupled to superior vertebrae 102 and inferior vertebrae 104 to facilitate fusion. In this case, a pedicle screw may be threaded into the vertebral body, such as pedicle screw 118 shown threaded into the pedicle of superior pedicle 102 in FIG. 1. Typically, two (2) pedicle screws 118 are used on each vertebral body although only one is shown on the superior vertebrae for convenience. To facilitate fusion, rods are connected to pedicle screws 118 in a conventional manner, not shown or further described as it is generally well known in the art.

As can be appreciated, the surgeon performing the surgical procedure needs to take great care to avoid injury to spinal cord 108 and/or nerves 110. The technology of the present application provides orientation and safety features for the surgeon which may reduce the time the surgeon needs to enter the space associated with intervertebral disc 106 and reduce the potential for injury to spinal cord 108 and/or nerves 110. Moreover, the technology of the present application provides a platform to allow the surgeon the ability to remove bone associated with the vertebral body and access the disc space in a reproducible and standardized fashion. Thus, the technology described herein may reduce the overall surgical time, provide the ability for surgeons to avoid damage to the patient, and ultimately lead to increased acceptance of minimally invasive fusion technology, for example.

Figure 3:
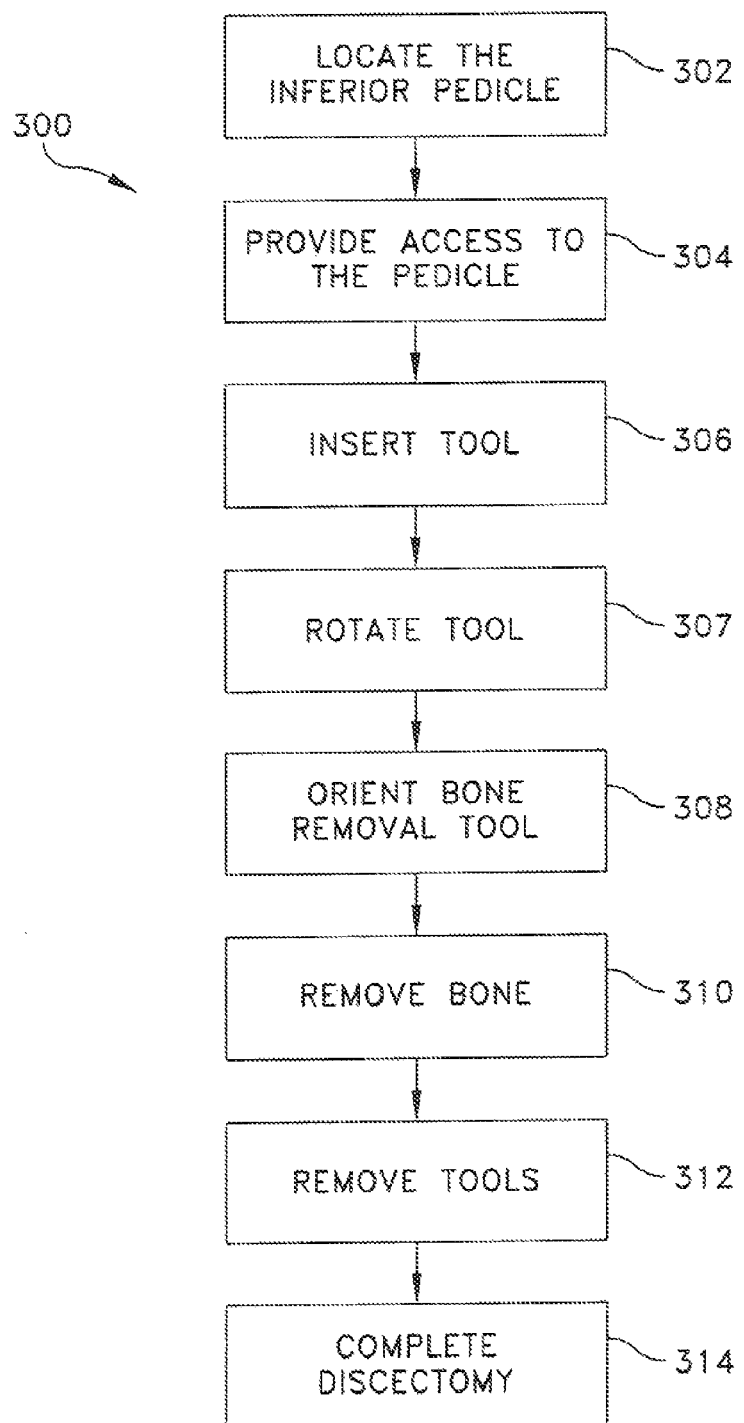
FIG. 3 is a flowchart illustrative of the surgical methodology consistent with an embodiment of the present disclosure.
Figure 4:
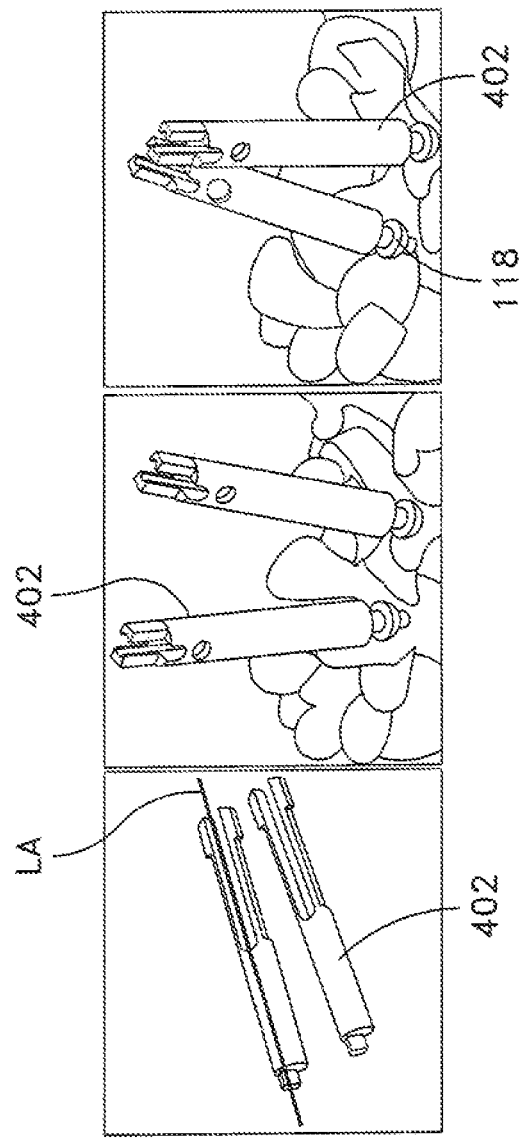
FIG. 4 is a view of pedicle screw extensions.
Figure 5:
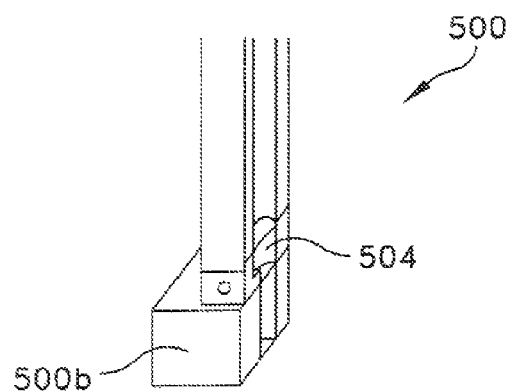
FIG. 5 is a perspective view of a part consistent with an embodiment of the present disclosure.
Figure 6:
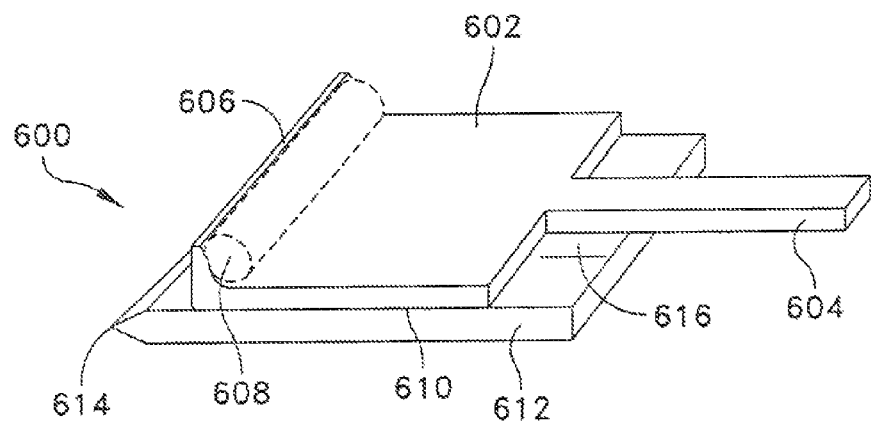
FIG. 6 is a perspective view of a speculum consistent with an embodiment of the present disclosure.

Turning now to FIG. 3, a flowchart 300 illustrating a method of the present disclosure will be described. For convenience, flowchart 300 relates only to use of the exemplary embodiment and does not address conventional surgical procedures, such as for a TLIF procedure. First, the surgeon may use conventional methods to cannulate the inferior pedicle 116, step 302. For example, the surgeon may use conventional guide wires and conventional surgical navigation technology to locate the inferior pedicle 116. Once the surgeon locates inferior pedicle 116, a dilator placed over the guide wire provides access to the pedicle, step 304. A pedicle screw 118 and extender 402 (see FIG. 4), as are generally known in the art, may be threaded into inferior pedicle 116. If a pedicle screw 118 and extender 402 are not used, an alternative structure may be placed that locates the pedicle and provides a track or stable platform. In alternative embodiments, the retractor systems described in conjunction with FIGS. 7-44 may be used to locate and attach to the pedicle.

After pedicle screw 118 and extender 402 or some other similar structure is provided, the surgeon would insert a bone cutter guide 500a and bone cutter 500b (collectively part 500), as shown bone cutter 500b is attached to bone cutter guide 500a as a unitary member. Part 500 has a track or groove 502 that can clamp on, for example, extender 402. Part 500 movably couples to extender 402 or some similar structure. The movable connection could be slidable, geared, rotational, or the like. Part 500 would be moved along extender 402 using the track or groove 502 until bone cutter 500b abuts a portion of the vertebral body, step 306. In some instances, it is likely the tool will need to be rotated or angled (medially and laterally) about the long axis LA (FIG. 4) of the extender to properly align the bone cutter 500b. As shown, bone cutter 500b is a simple box shape. Other shapes are possible, such as, for example, a wedge shape, a circular shape, a conical shape, other random shapes, or the like.

Once placed next to the vertebral body, bone cutter 500b may need to be angularly oriented. Optionally, part 500 may have an angular orientation device 504 to align bone cutter 500b with the portion of the vertebral body to be removed. Angular orientation device 504 may be a simple cam, hinge or the like. If angular orientation is necessary, the device is oriented as necessary, step 308. Once oriented, the surgeon uses the bone cutter 500b to remove portions of the vertebral body consistent with conventional surgical procedures, step 310, such as, for example, the surgeon may remove a portion of the facet joint. Bone cutter 500b may be shaped in a box shape as is conventional or other shapes, such as, circular, rectangular, triangular, other geometric or random shapes. Bone cutter 500b is used to remove a portion of the vertebral body only as necessary. If bone cutter 500b is hollow or has a through hole, bone cutter 500b may remain in place, but is preferably removed, step 312. A speculum 600, having a substantially flat portion 602 and handle 604, is inserted into the disc annulus, step 312. Flat portion 602 may terminate in a lip 606. Once placed, speculum 600 is moved towards the superior vertebrae 102. Flat portion 602 and, if provided, lip 606, push on nerve 608 (shown in phantom, which corresponds to nerve 110) and holds nerve 608 against the superior pedicle 102. Underside 610 of speculum 600 provides a shield as the surgeon accesses the space associated with intervertebral disc 106. Once speculum 600 is placed such that nerve 608 is removed from the surgical area, the surgeon can complete the operation, step 314. Optionally, speculum 600 may have a distractor 612, which may take many shapes but is generally flat and long, similar to flat portion 602. Distractor 612 may extend beyond flat portion 602 and terminate in a leading edge 614. Leading edge 614 may pierce the disc annulus to provide a platform or base for the surgical sight. Speculum 600 may be placed to maintain separation of vertebral bodies to facilitate access to the space associated with intervertebral disc 106. Distraction or separation of distractor 612 and flat portion 602 may be obtained by, for example, turning a cam 616, a scissor operation, or the like. Other exemplary embodiments are illustrated in FIGS. 7-44. These illustrations provide various device configurations and procedures in connection with a retractor system 700 for providing a surgical pathway to a spinal site using a pedicle guided retractor system.

Figure 7:
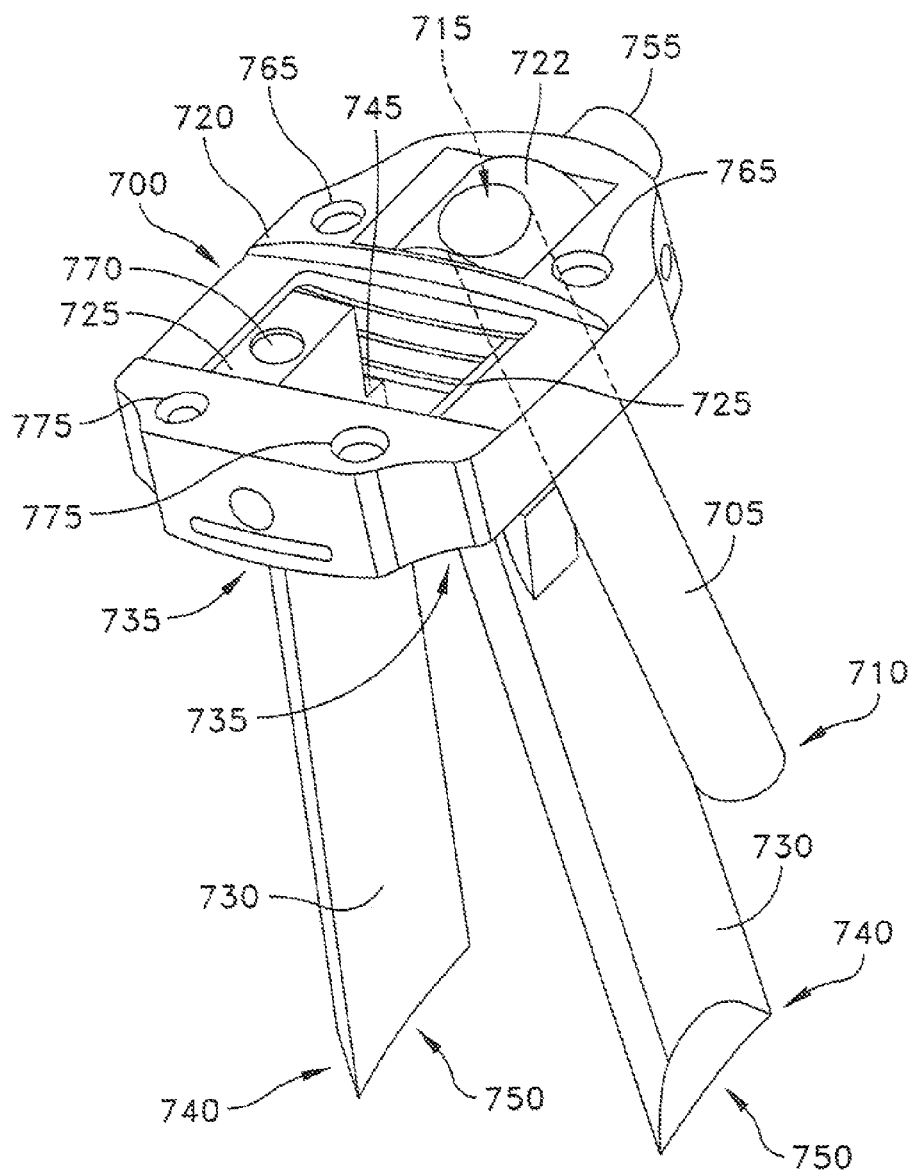
FIG. 7 is a perspective view of a portion of a retractor system consistent with an embodiment of the present disclosure.
Figure 8:
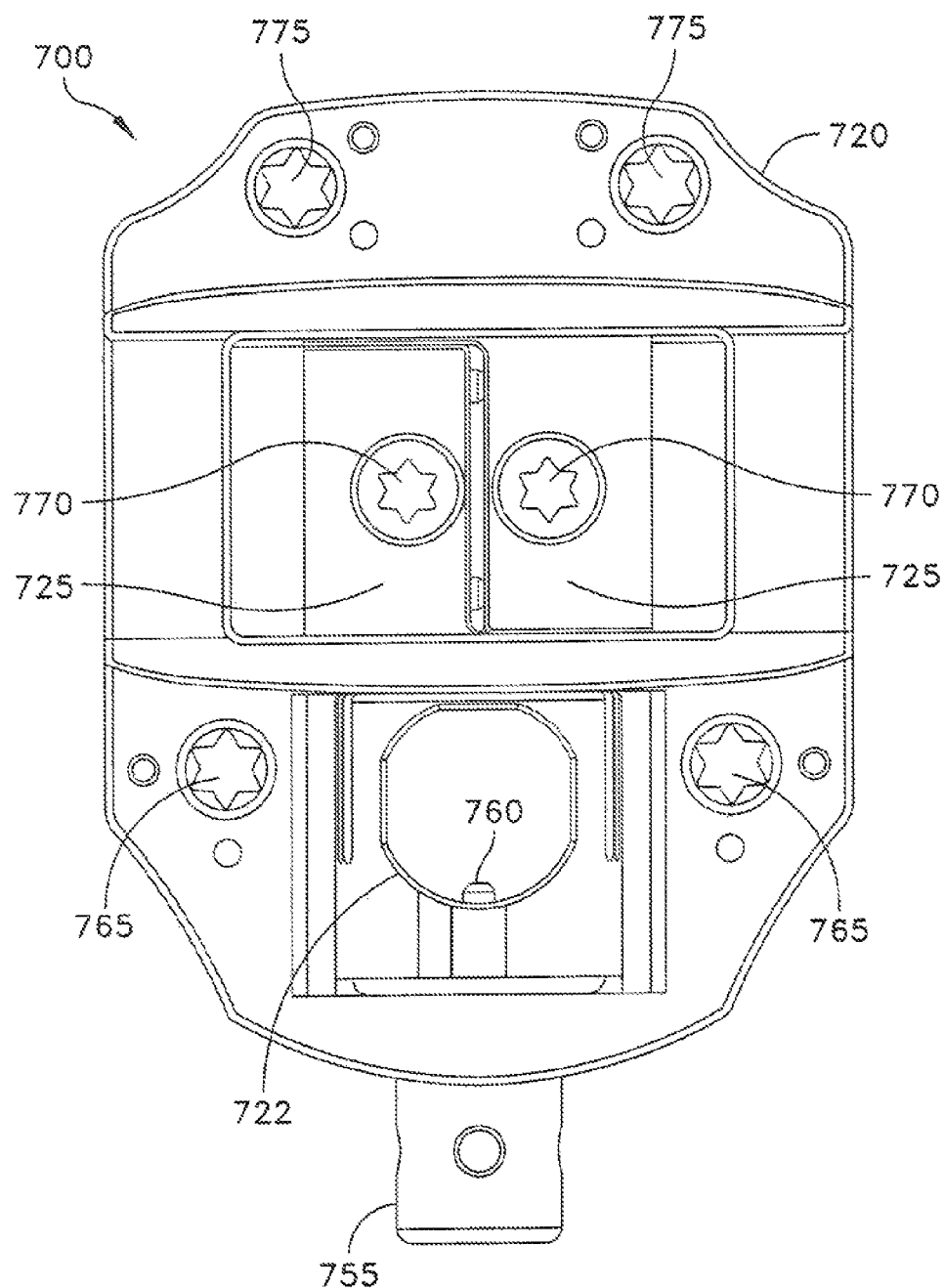
FIG. 8 is a proximal plan view of the retractor system of FIG. 7.
Figure 9:
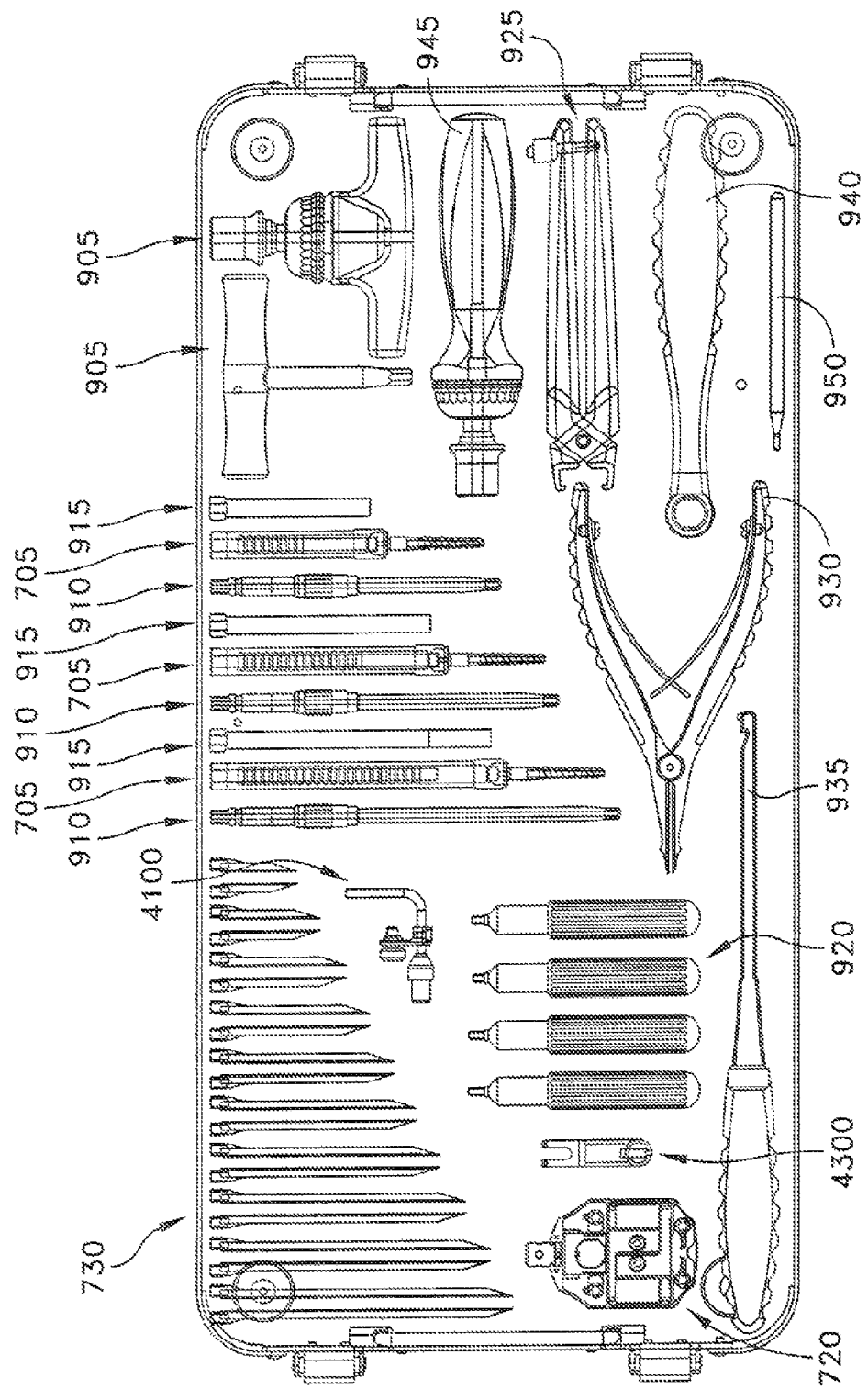
FIG. 9 is an illustration of a surgical kit containing the retractor system of FIG. 7.

As illustrated in FIGS. 7-9, retractor system 700 may include an elongate member, such as a post 705 having a distal end 710 and a proximal end 715. Distal end 710 of post 705 may have an anchor 1300 (see FIG. 13) to attach post 705 to a pedicle 2500 (see FIG. 25) of a vertebral body 2505 with respect to an intervertebral disc 2510 so as to be configured to facilitate surgical access to intervertebral disc 2510 between vertebral body 2515 and vertebral body 2505. Post 705 may, in some embodiments, be or include the extender 402 (see FIG. 4).

Figure 7A:
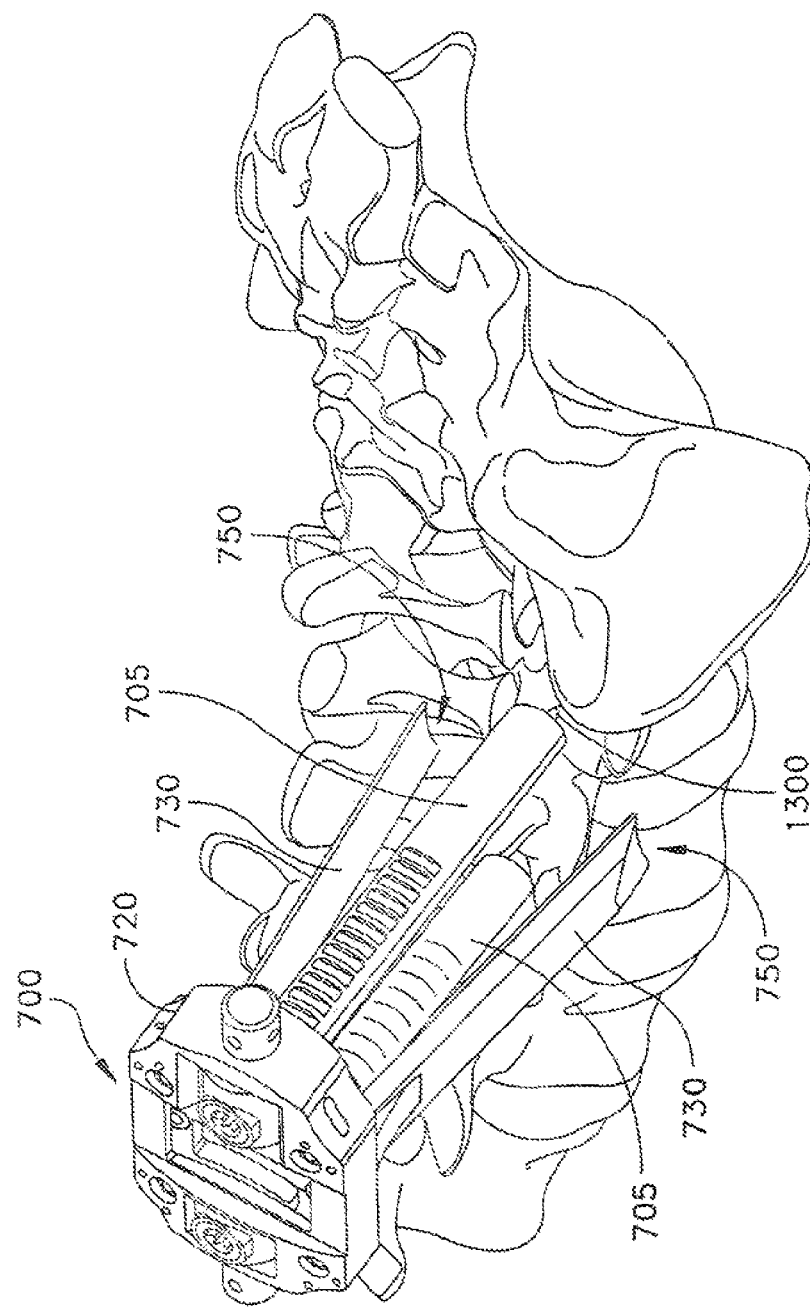
FIG. 7A is a perspective view of a portion of a retractor system with first and second posts.

While retractor system 700 is generally shown using a single post 705 to couple to an inferior pedicle 2500, it is possible to provide a retractor system 700 such that the single post 705 is coupled to a superior pedicle as a matter of design choice, although it is believed that coupling the post 705 to the inferior pedicle provides improved access to the surgical area. Alternatively to using a single post 705, retractor system 700 may comprise first and second posts 705 (see FIG. 7A.) In this alternative construction, the first post 705 may be coupled to the inferior pedicle and the second post 705 may be coupled to the superior pedicle. One advantage of using a first post and second post 705 would include providing a retractor system 700 that could operate to distract or compress the vertebrae as desired by the surgeon.

Retractor system 700 may include a retractor body 720 having a collar 722 to adjustably attach retractor body 720 to post 705 between distal end 710 and proximal end 715 of post 705. A pair of slides 725 may adjustably couple to retractor body 720. Slides 725 may be configured for selective adjustment with respect to one another between a substantially closed position (see FIG. 8C) and an opened position (see FIG. 8D) with slides 725 further apart than the substantially closed position. Slides 725 may be adjustably coupled to retractor body 720 using a tongue and groove, slot and channel, or other adjustable connections as are generally known in the art.

A pair of blades 730 may be mounted to slides 725. Each one of blades 730 may have a proximal end 735 and a distal end 740. A distance between proximal end 735 and distal end 740 of each one of blades 730 may be configured for displacing tissue for access to an intervertebral disc. Depending on the patient size and other factors, different length blades 730 can be selected and used. An attachment portion 745 may be positioned adjacent the proximal end 735 of each one of blades 730 for attaching one of slides 725 thereto. A geometry 750 of distal end 740 of each one of blades 730 may be provided for conforming to anatomy surrounding the pedicle (e.g., pedicle 2500). For example, geometry 750 may include a region of blade 730 having diminished thickness or varying thickness. Geometry 750 may further or alternatively include a flat or curved distal edge of blade distal end 740.

Figure 7B:
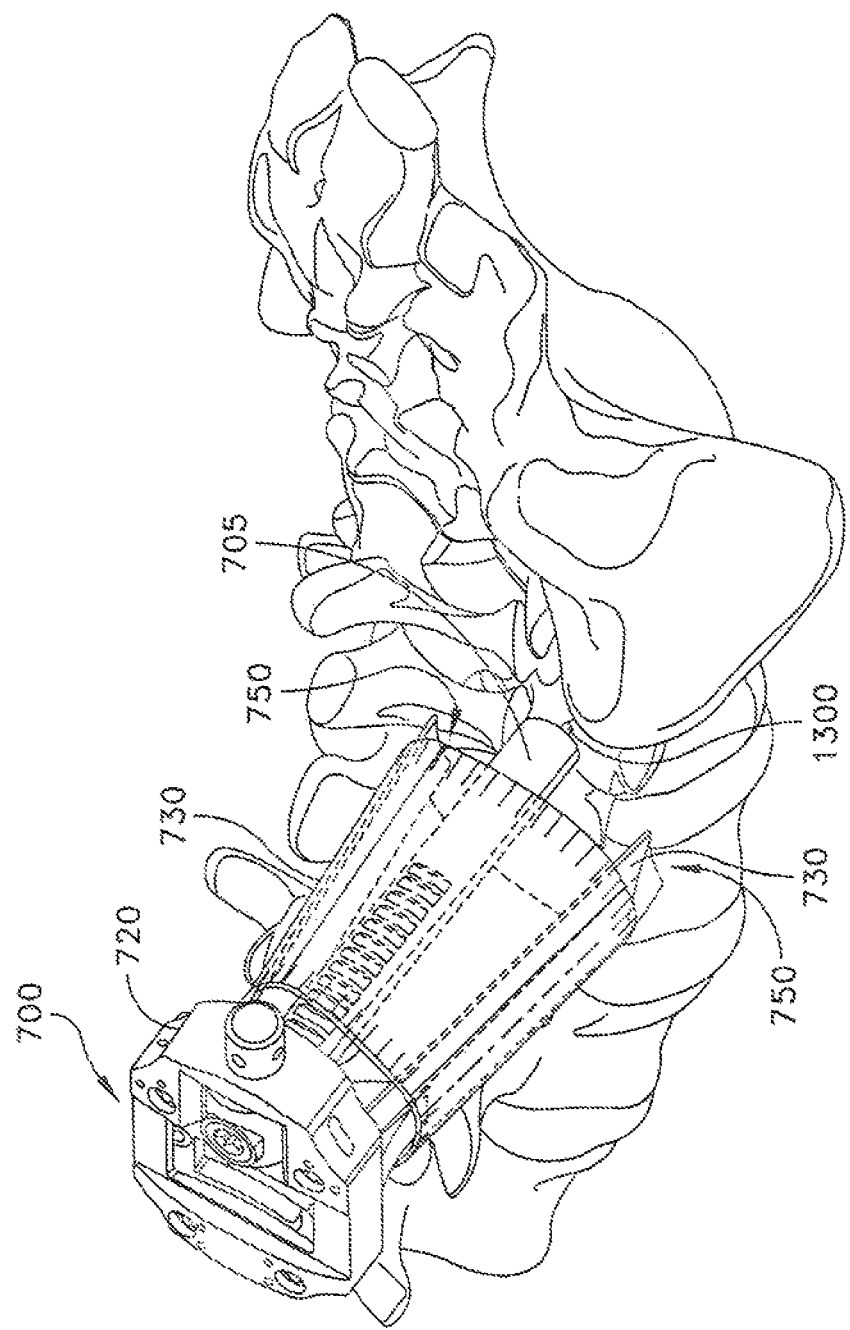
FIG. 7B is a perspective view of a portion of a retractor system with a shroud that inhibits soft tissue from interfering with the surgical area.

With reference to FIG. 7B, in certain embodiments it may be desirable to provide a shroud 752, shield or some other device that inhibits soft tissue from interfering with the surgical area. The shroud 752 may be expandable such that it can be fitted around, for example, the blades 730 prior to implanting the retractor system 700 into a surgical area and the shroud 752 expands as the blades move apart to establish the surgical area. Alternatively, the shroud 752 may be a relatively rigid shroud 752 that may be fitted about the body and post of the retractor system after the blades establish the surgical area. The shroud 752 may provide a generally constant diameter opening to the surgical site. In an alternative embodiment, the shroud 752 has a larger opening at the distal end (e.g., adjacent the disc space) than at the proximal end (e.g., outside the patient). Still further, the shroud 752 may be fitted about post 705 (or posts 705) and blades 730. An example of an expandable shroud is contained in U.S. Pat. No. 7,056,321 titled "Method of Securing Vertebrae" issued to Pagliuca et al. on Jun. 6, 2006, at FIGS. 33-45 and corresponding text. U.S. Pat. No. 7,056,321, is incorporated herein by reference as if set out in full herein.

In one embodiment, a post tightening knob 755 may interoperate with collar 722, which in turn adjusts the position of a protrusion 760 (see FIG. 8) within collar 722. Protrusion 760 may provide a selective engagement to hold post 705 within collar 722. One or more pitch/roll dials 765 may be provided in retractor body 720 to control the orientation of the retractor body 720 relative to the post 705. A blade tightening screw 770 may be provided in communication with each one of slides 725 to selectively secure and release blades 730 from retractor body 720. A slide lock 775 may be provided in communication with each one of slides 725 to selectively lock and release each of slides 725 with respect to retractor body 720. In an alternative embodiment, slides 725 are engagingly coupled together in a manner which allows both slides 725 to be locked in place relative to one another with the use of a single slide lock 775.

In one embodiment, one or more of pitch/roll dials 765, blade tightening screw 770, and slide lock 775 may include a ratchet adjustment for its respective operation. For example, and in an embodiment, rotating a Torx drive in a desired direction, such as towards a laser marked dot, operates to lock or fix the feature it controls. Rotating a Torx drive in a different or same desired direction, such as towards a laser marked circle, operates to unlock or release the feature it controls. In another embodiment, one or more of pitch/roll dials 765, blade tightening screw 770, and slide lock 775 may include another adjustment mechanism for its respective operation.

Looking now at FIG. 9, and in an embodiment, there is shown an exemplary version of a surgical kit 900 containing components of an embodiment of retractor system 700. Kit 900 may contain one or more posts 705, retractor body 720, blades 730, one or more T-handles 905, a driver 910 for post 705, a pressure core 915 for post 705, one or more blade and retractor straight handle drivers 920, an inserter 925, a muscle spreader 930, a muscle splitter 935, a counter torque instrument 940, a straight handle driver 945, a turning rod 950, a light source 4100, and a snake arm connector 4300. In alternative embodiments, the type, quantity and location of components within kit 900 may vary from that depicted in FIG. 9. For example, blades 730 of varying lengths may be provided within kit 900.

In exemplary embodiments, there are provided methods of facilitating surgical access to a vertebral disc. In one embodiment, a method may include the steps of establishing a soft tissue path with an incision to a vertebral disc, determining a location of an inferior pedicle, placing a k-wire at the inferior pedicle, dilating soft tissue adjacent the inferior pedicle, attaching a post to the inferior pedicle, choosing a pair of blades that match a depth indicated by the post, securing each one of the pair of blades to a retractor body, driving the blades into the incision and sliding the post through a collar of the retractor body, securing the retractor body to the post, and opening the blades to form a surgical opening to access a vertebral disc. FIGS. 10-40 illustrate various embodiments of methods of facilitating surgical access to a vertebral disc.

Figure 10:
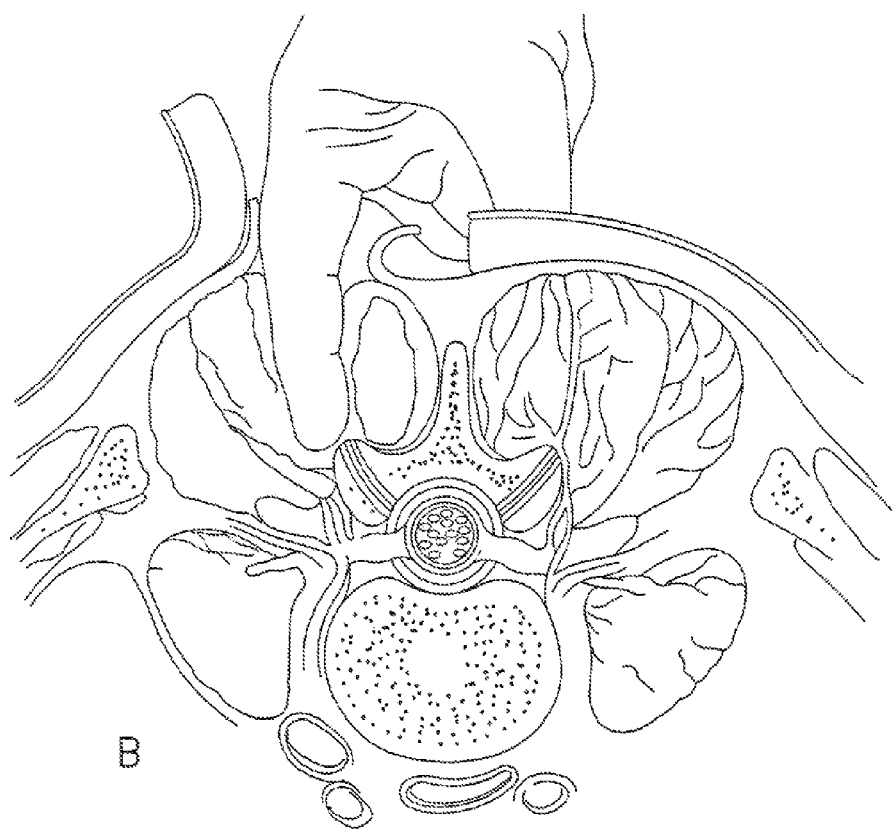
FIG. 10 is a view of a patient prior to insertion of the retractor system of FIG. 7.

In some embodiments, as shown in FIG. 10, a soft tissue path is established. Using a paraspinal approach, such as a modified Wiltse approach, an appropriate length skin and fascial incision may be made to establish a muscle plane path. In some embodiments, the incision is approximately 35 mm in length, and is made approximately 40 mm from the midline.

Figure 11:
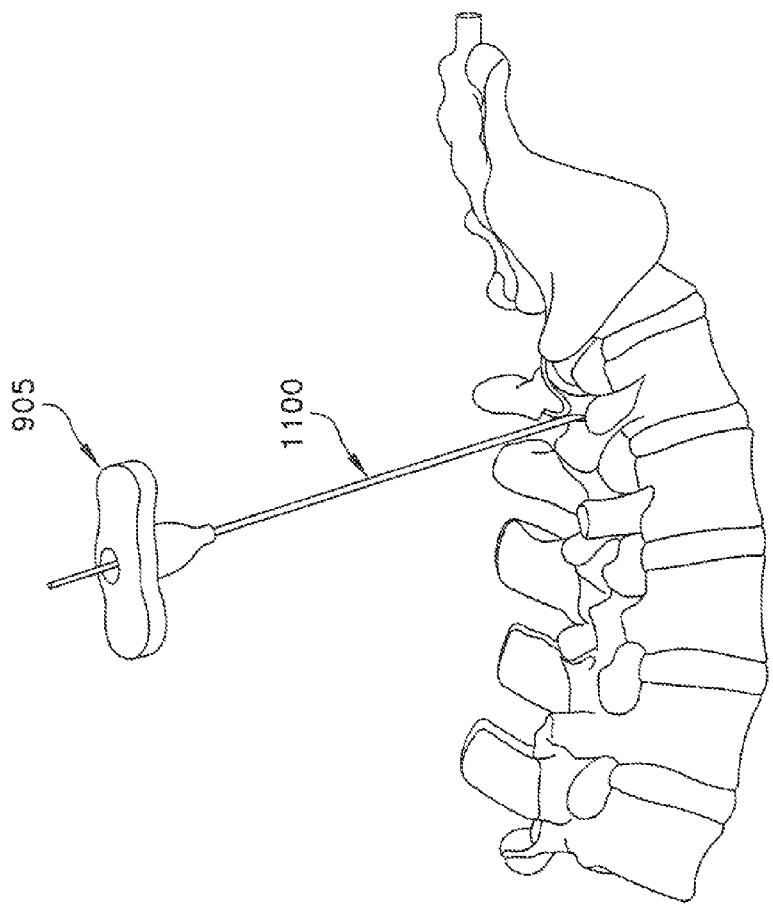
FIG. 11 is a perspective view of a spine accessed by a Jamshidi needle.
Figure 12:
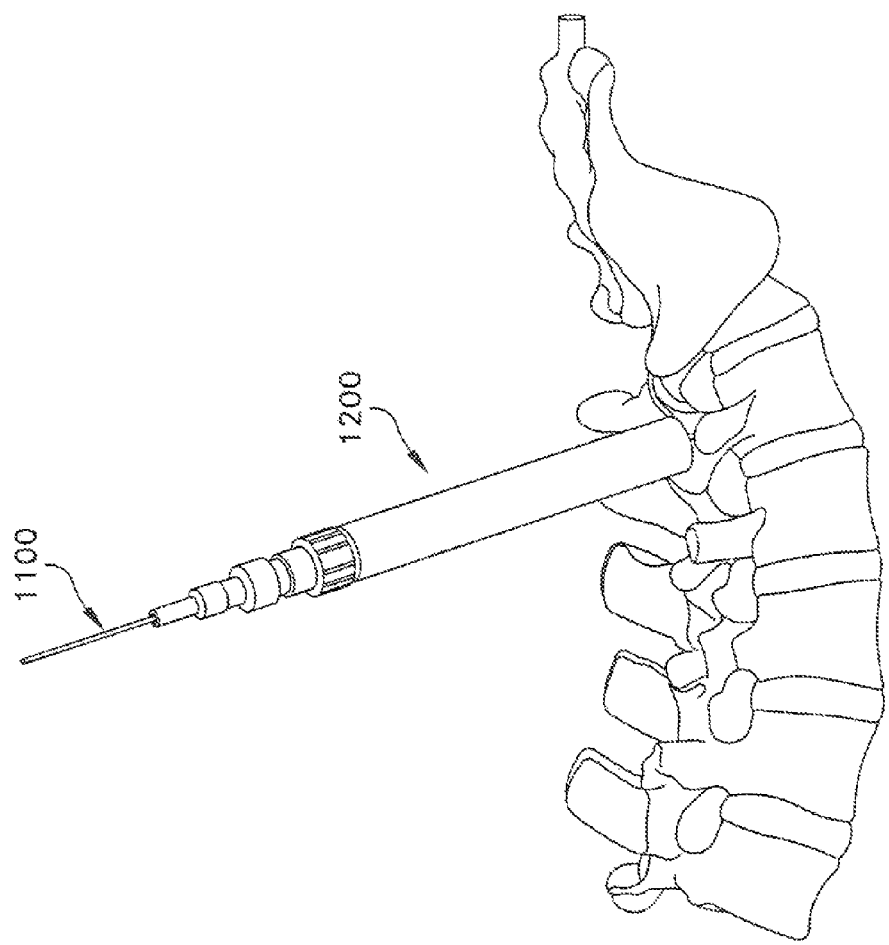
FIG. 12 is a perspective view of a spine accessed by a series of dilators of the retractor system of FIGS. 7 and 9.
Figure 13:
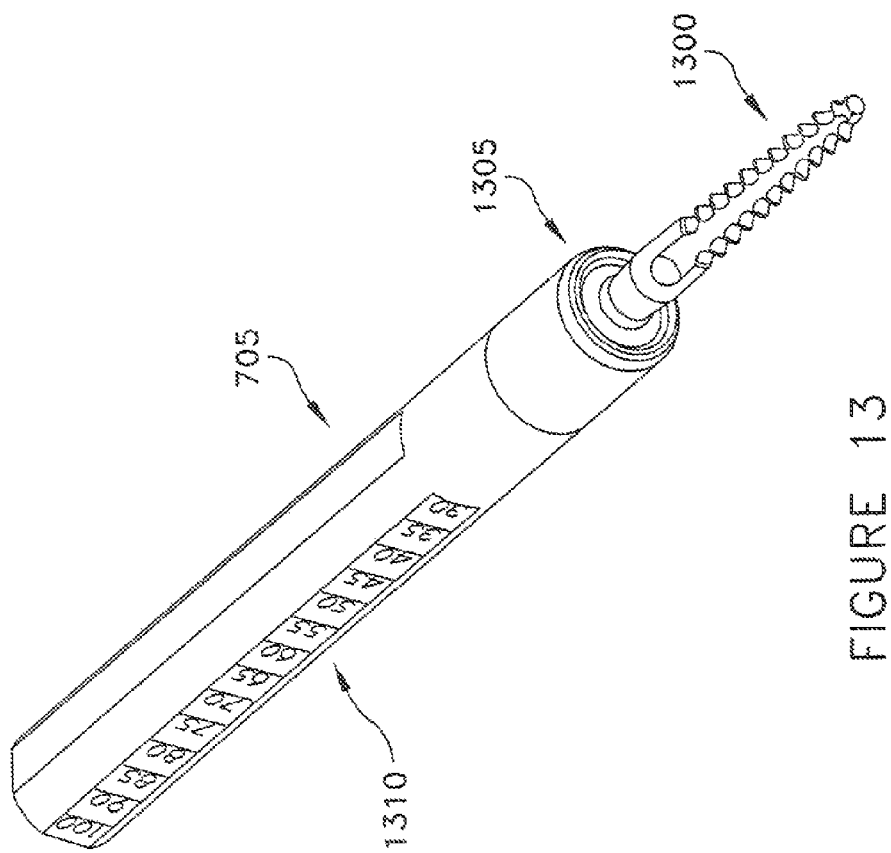
FIG. 13 is a perspective view of a post of the retractor system of FIGS. 7 and 9.
Figure 14:
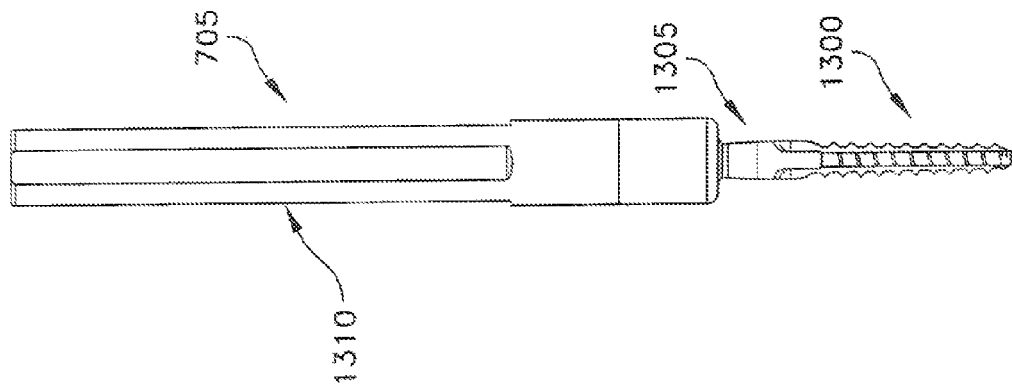
FIG. 14 is an elevation view of the post of FIG. 13.
Figure 15:
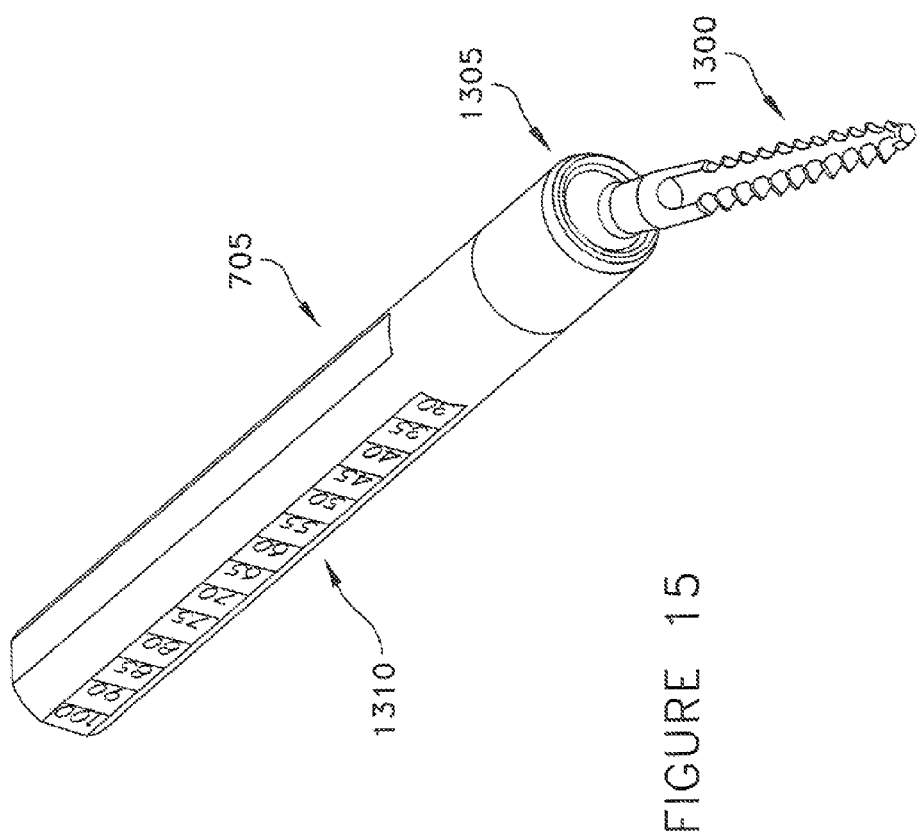
FIG. 15 is a perspective view of the post of FIG. 13 showing an anchor at an alternative angle.

Next, the pedicle location may be determined as indicated in FIG. 11. For example, under fluoroscopic guidance an instrument, such as a bone marrow biopsy needle (e.g., a Jamshidi needle), is used to locate and cannulate the inferior pedicle on the same side the TLIF will be performed. The inner stylus is removed and a K-wire 1100 is inserted to the appropriate depth using a T-handle inserter 905.

Soft tissue dilation may be performed using K-wire 1100 positioned in place. Keeping K-wire 1100 steady, concentric sized dilators 1200 (e.g., starter, second, third, and final dilators) are inserted over K-wire 1100 (see FIG. 12). Once the final dilator has been placed, which in some cases is the third dilator, all inner dilator tubes may be removed, leaving only the final dilator in place. This final dilator 1200 can maintain a working window for at least some of the following procedures.

Figure 16:
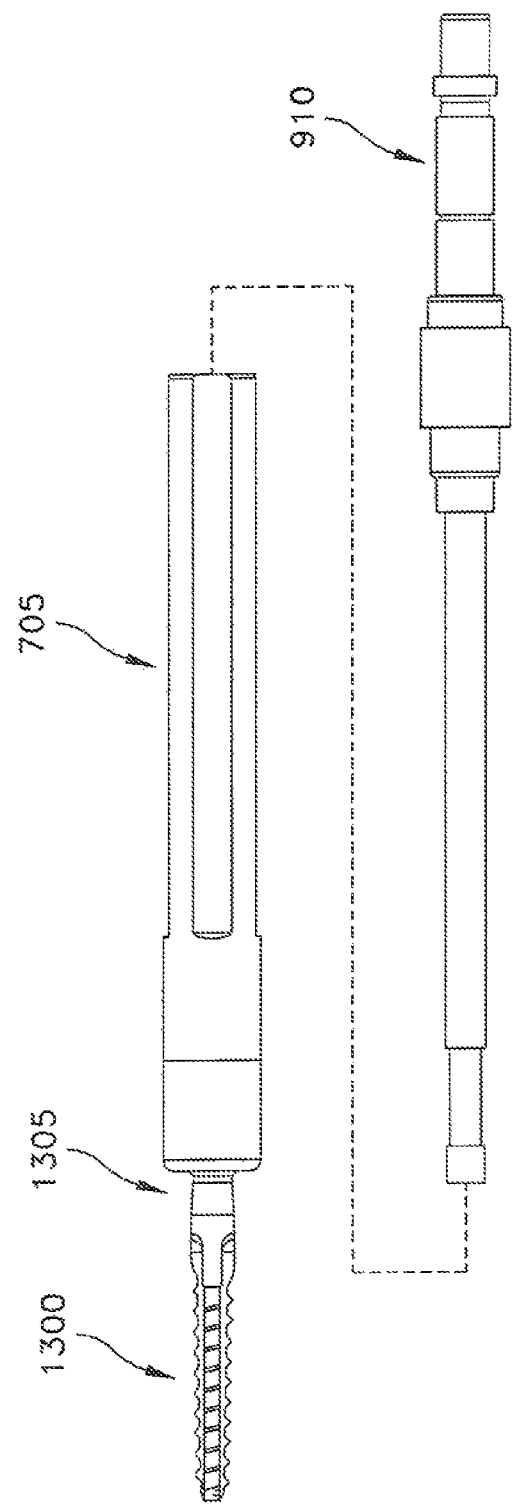
FIG. 16 is an elevation view of the post of FIG. 13 and a driver of the retractor system of FIGS. 7 and 9.
Figure 16A:
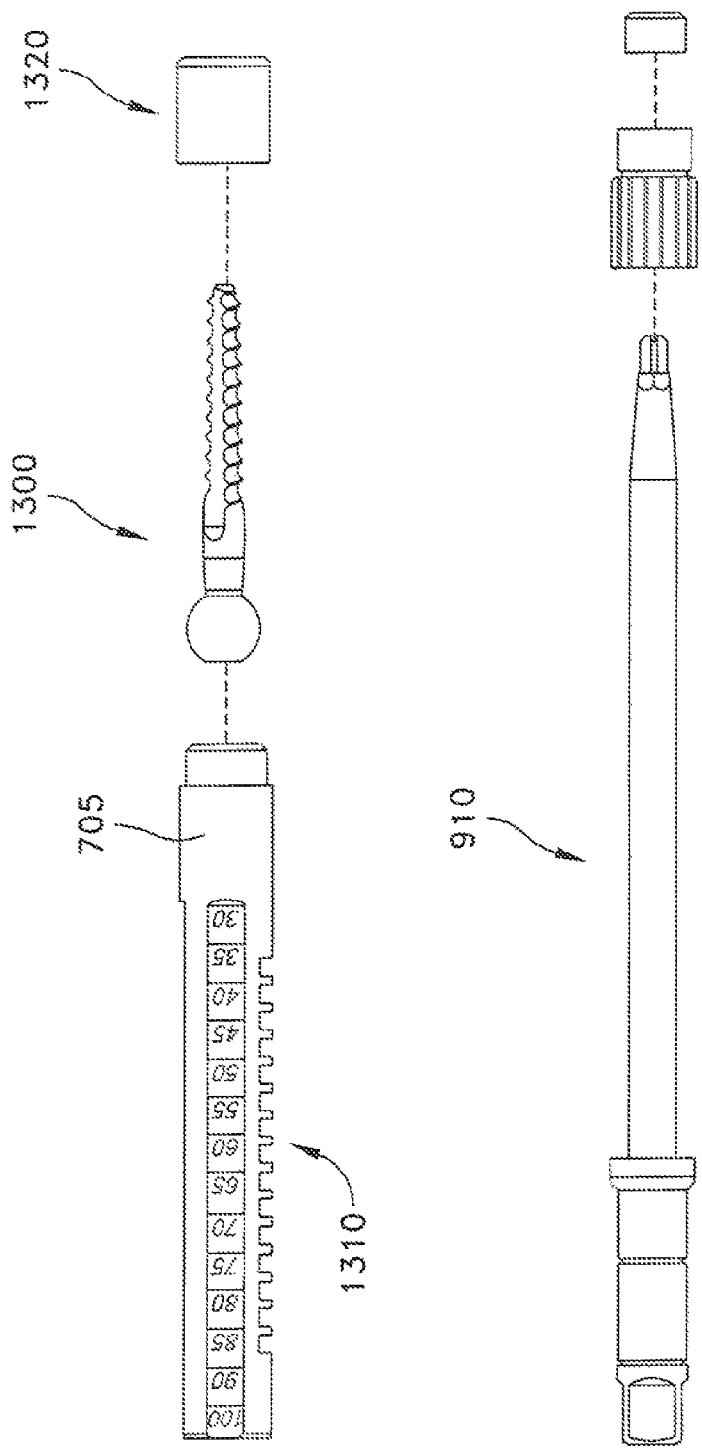
FIG. 16A is an exploded view of the post and driver of FIG. 16.
Figure 17:
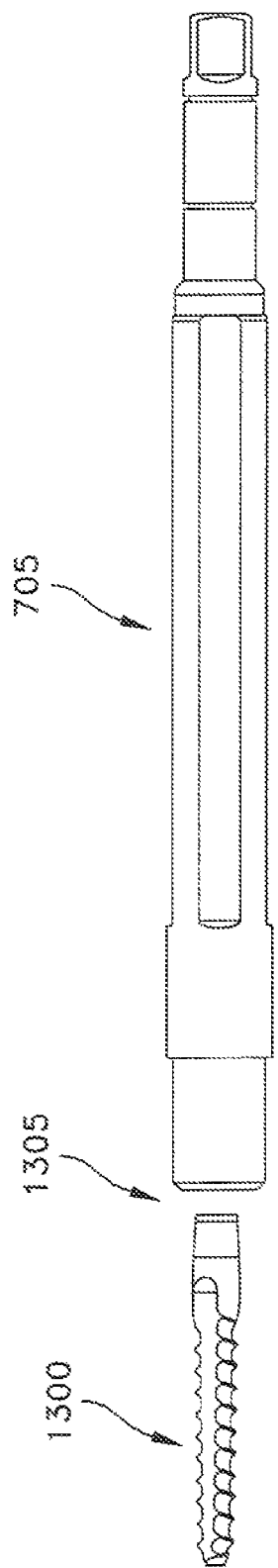
FIG. 17 is a view of the post and driver of FIG. 16 assembled together.
Figure 18:
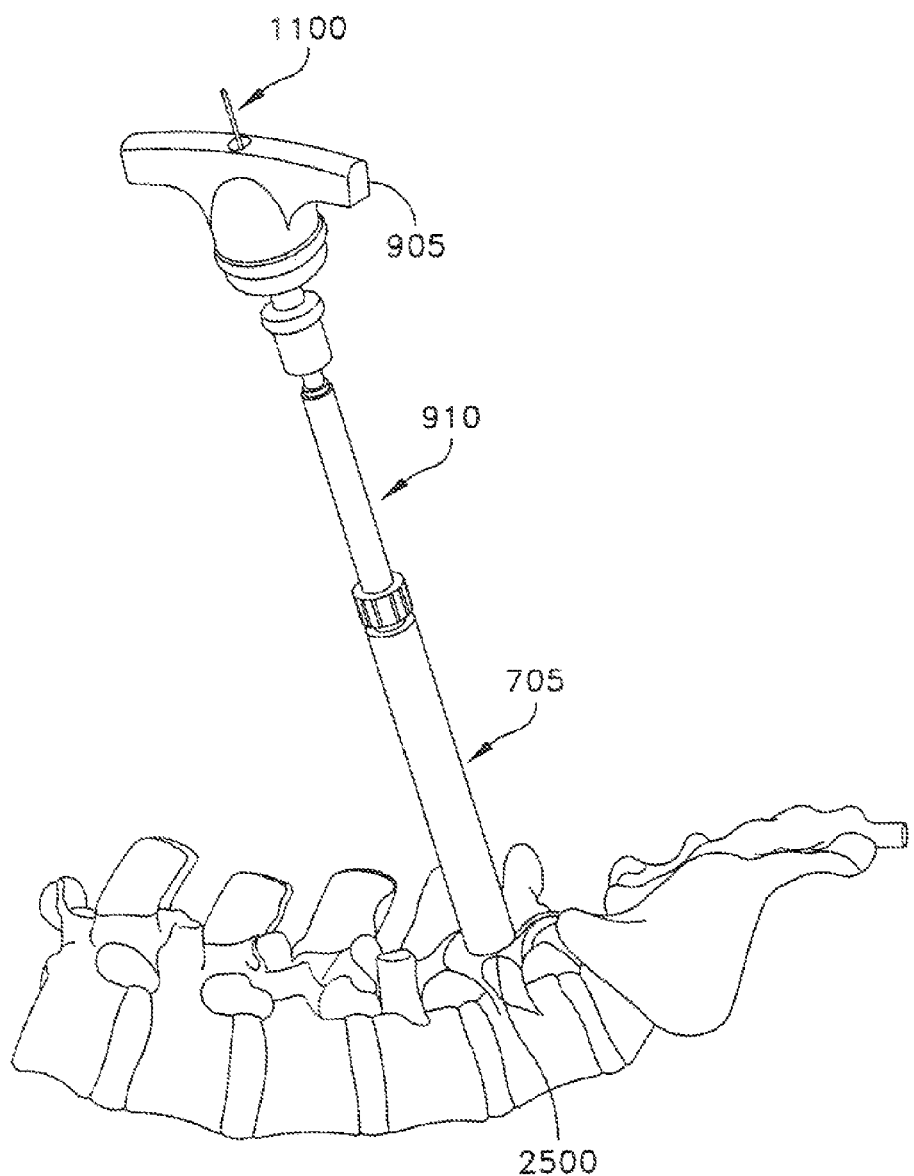
FIG. 18 is a perspective view of a spine accessed by the post, driver, and a T-handle inserter of the retractor system of FIGS. 7 and 9.

FIGS. 13-18 illustrate preparation and attachment of an elongate member such as a post 705 to a pedicle. Post 705 may form a polyaxial (e.g., FIG. 16A) or mono axial (e.g., FIG. 17) joint 1305 with anchor 1300. In the embodiment shown in FIG. 16A, a collar 1320 is coupled to post 705 in a manner which secures anchor 1300 to post 705 while allowing rotational and pivoting movement of anchor 1300. Collar 1320 may be coupled to post 705 by welding, adhesives, or other appropriate coupling techniques.

Ribs 1310 may be provided on post 705 for interaction with protrusion 760 in collar 722 of the retractor body. In some embodiments, ribs 1310 have numerical or other indicators so the height or location of attachment of collar 722 can be determined relative to anchor 1300. Protrusion 760 may be selectively positioned in ribs 1310 by adjusting post tightening knob 755.

Driver 910 is slid or translated along a cannula of post 705 and attached into place, such as by threading. Coupling driver 910 to post 705 operates, in some embodiments, to lock the angular relationship between anchor 1300 and post 705. For example, in some embodiments anchor 1300 comprises a polyaxial joint which allows rotational and pivoting movement between anchor 1300 and post 705. In some embodiments, driver 910 has a distal portion which engages a proximal portion of anchor 1300 to prevent the rotational and/or pivoting movements of anchor 1300. The engagement between driver 910 and anchor 1300 may include, for example, a frictional relationship between two similarly curved or shaped surfaces (e.g., a spherical head of anchor 1300 and a matching concave distal end of driver 910), or may include a projection and detent relationship, or may use other engagement relationships. In this manner, driver 910 may be used to drive, screw, or otherwise insert anchor 1300 into the vertebral body.

Post 705 and driver 910 are translated over K-wire 1100, with a straight handle driver 945, T-handle 905 or a similar device. Anchor 1300 (which may be configured as a post tap, such as a 4.5 mm or other length post tap) is then carefully driven into the pedicle. In a preferred embodiment, post 705 is driven into the pedicle, but does not bottom out against the pedicle or facet in order to prevent loss of polyaxial mobility with polyaxial joint 1305. In the event post 705 does bottom out against the pedicle or facet, in some embodiments post 705 is backed out, such as by using about 2 or 3 turns of driver 945 or handle 905.

Figure 19:
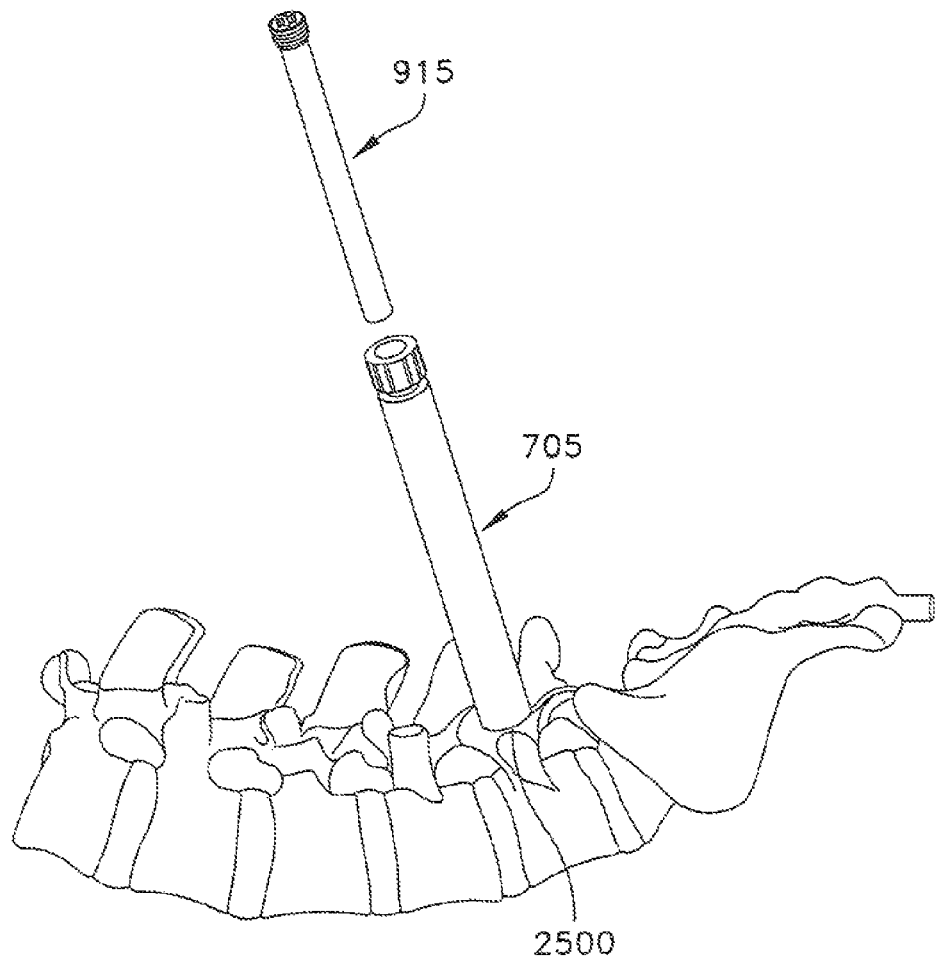
FIG. 19 is a perspective view of a spine accessed by the post and a pressure core.
Figure 20:
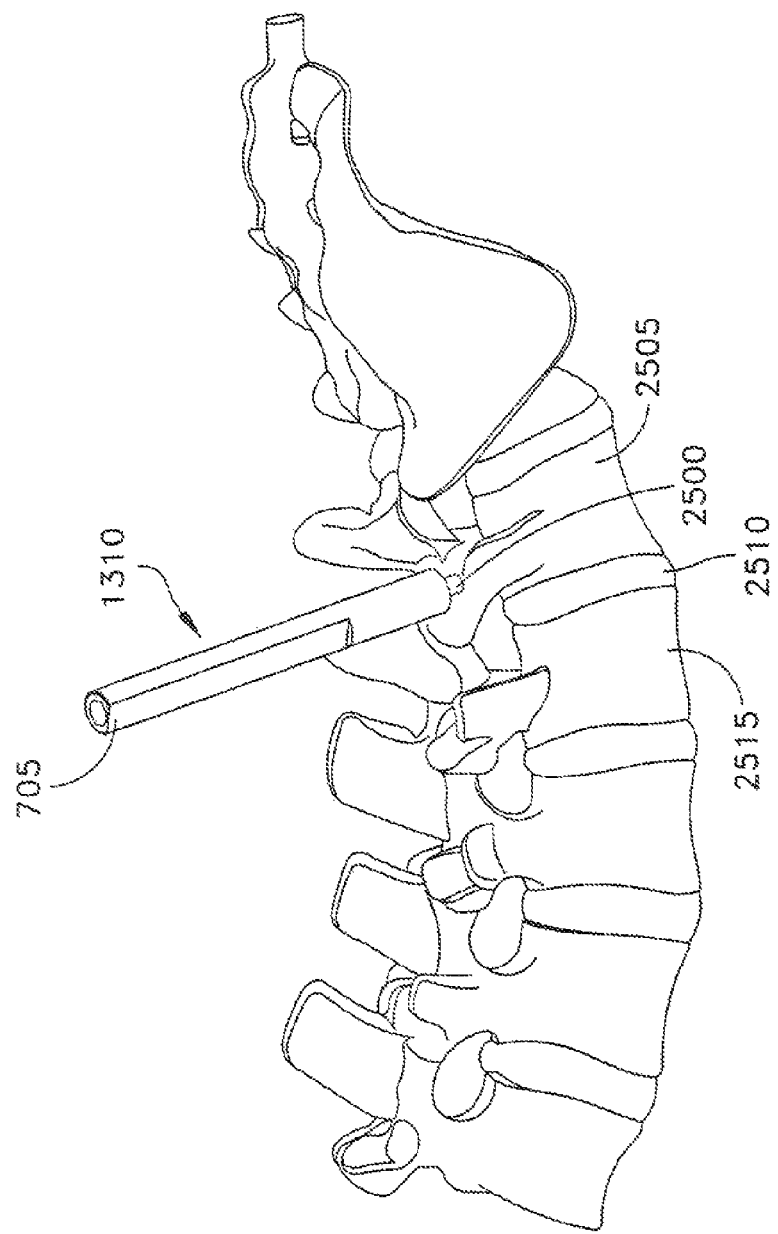
FIG. 20 is a perspective view of a spine accessed by the post.

Next, and as best illustrated in FIGS. 19 and 20, driver 910 is detached from post 705, K-wire 1100 is pulled out or extracted, and dilator 1200 is removed. A pressure core 915 is placed or slid down into post 705. Pressure core 915 may be tightened to post 705, such as by finger tightening. In some embodiments, post 705 is oriented such that ribs 1310 face away from the disc space. Properly positioned, post 705 should be secured to the pedicle but free to spin and pivot.

Figure 21:
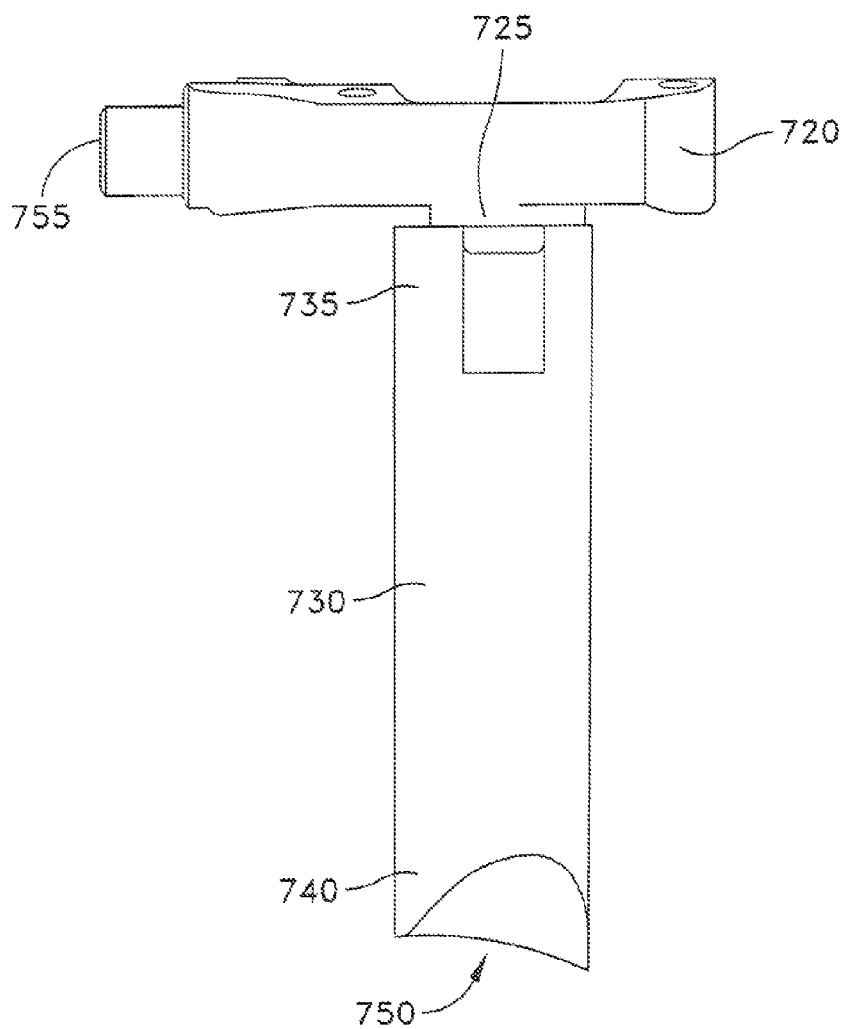
FIG. 21 is an elevation view showing blades coupled to slides of the retractor system of FIGS. 7 and 9.
Figure 22:
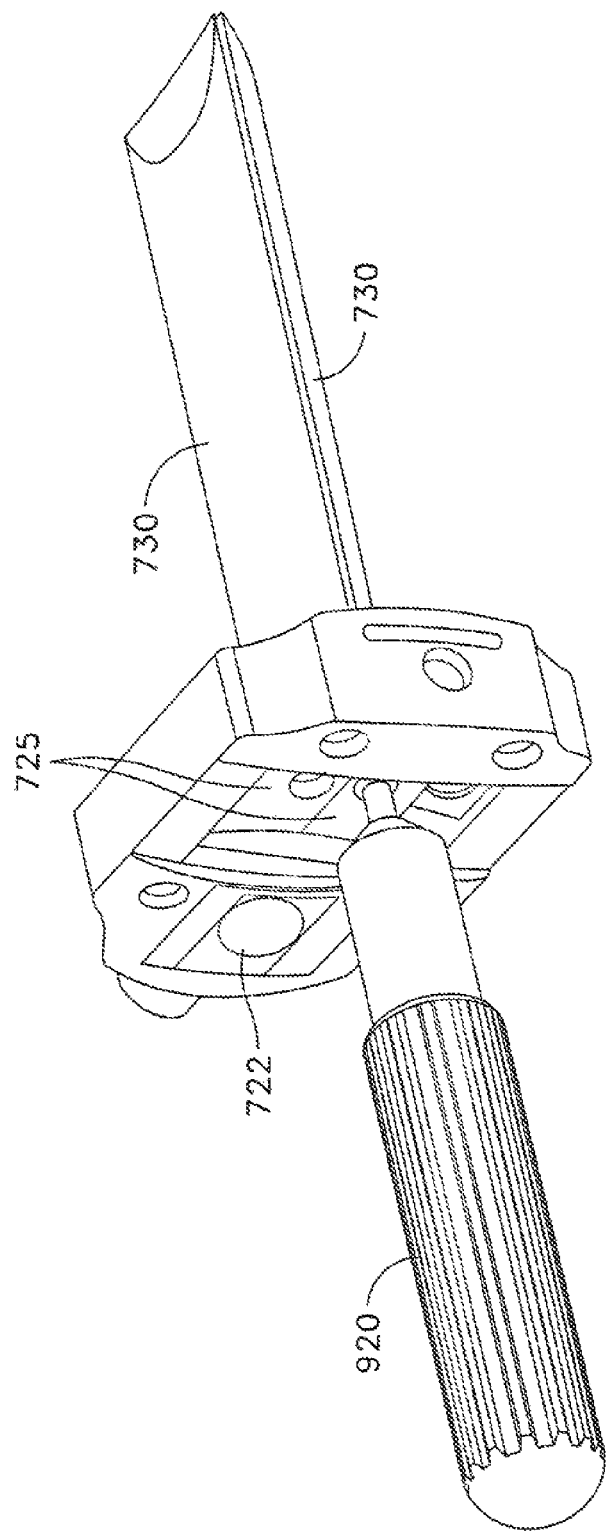
FIG. 22 is a perspective view of the assembly of FIG. 21 including a driver engaged therewith.

In an exemplary embodiment, retractor body 720 and blades 730 may be assembled together as described herein. With reference to FIGS. 21 and 22, from the sizes of blades 730 provided in kit 900, a pair of blades 730 may be chosen that match the depth indicated by post 705. This depth may be identified by the number on post 705 that appears just above the surface of the patient's skin. Using a driver, such as driver 920, which may be selected as a T15 Torx Driver 920, each blade 730 may be secured in the orientation shown and into the corresponding slot in retractor body 720. As previously discussed, blade tightening screw 770 may be turned to help hold or lock blade 730 in place, with it being desirable to avoid over-tightening blade tightening screw 770.

Figure 23:
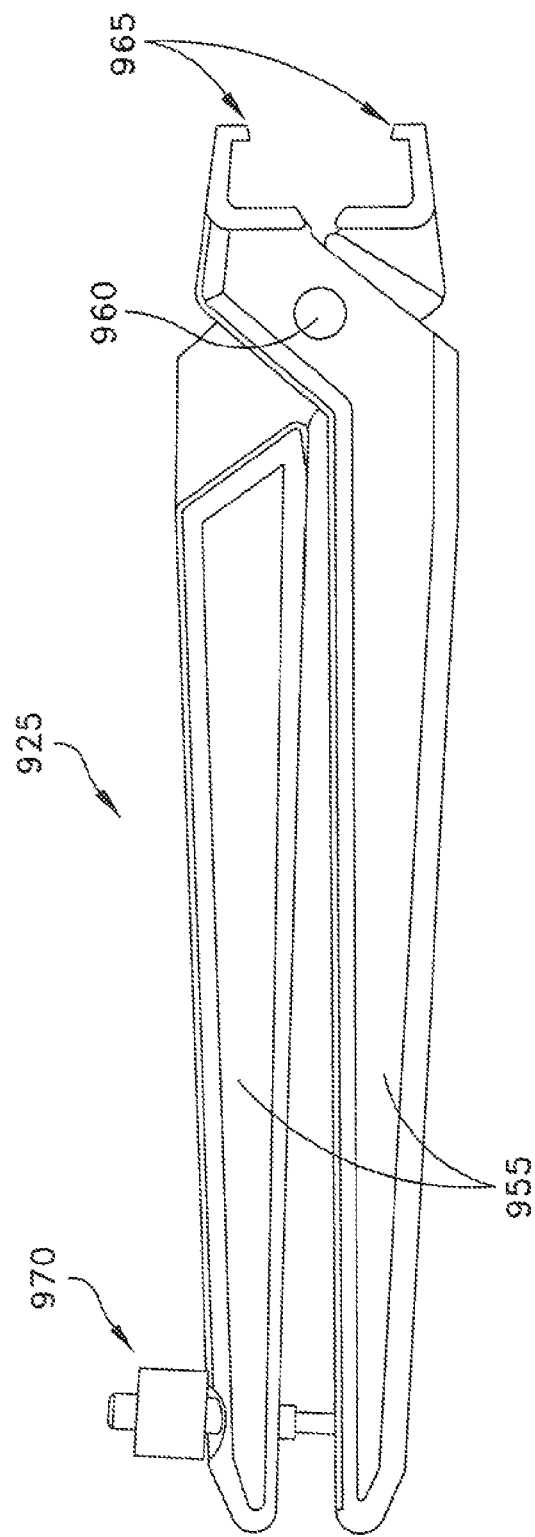
FIG. 23 is an elevation view of an inserter of the retractor system of FIGS. 7 and 9.
Figure 24:
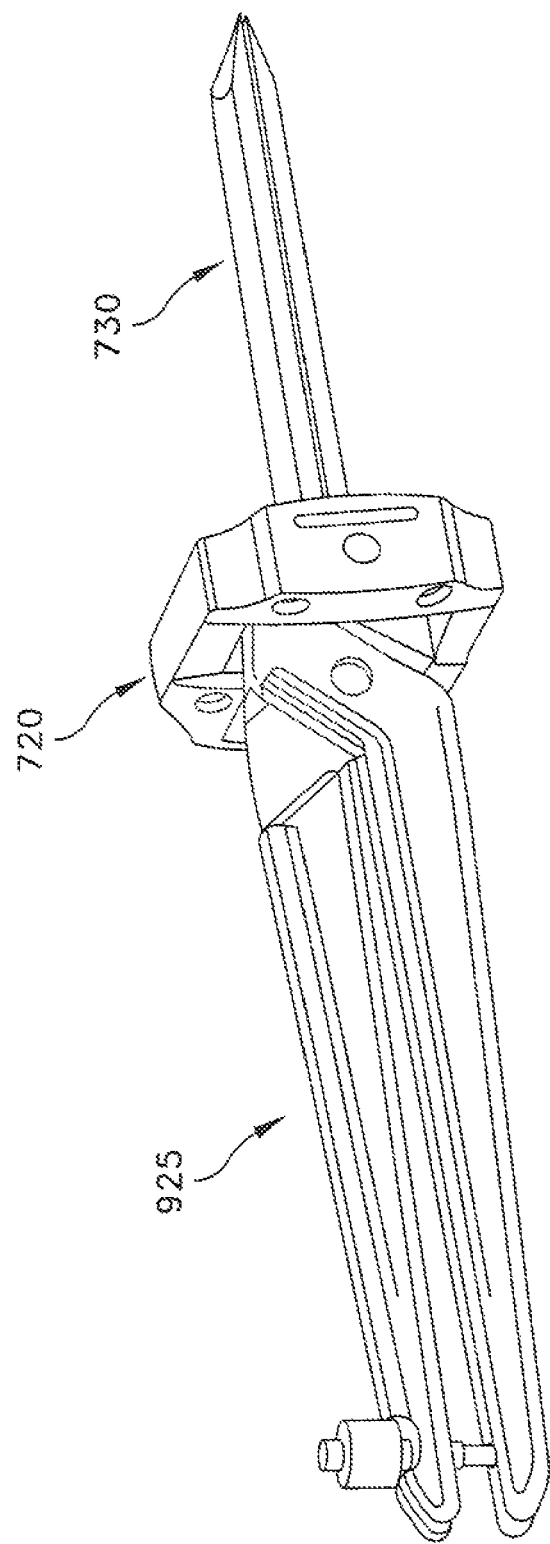
FIG. 24 is a perspective view of the retractor coupled to the inserter.
Figure 25:
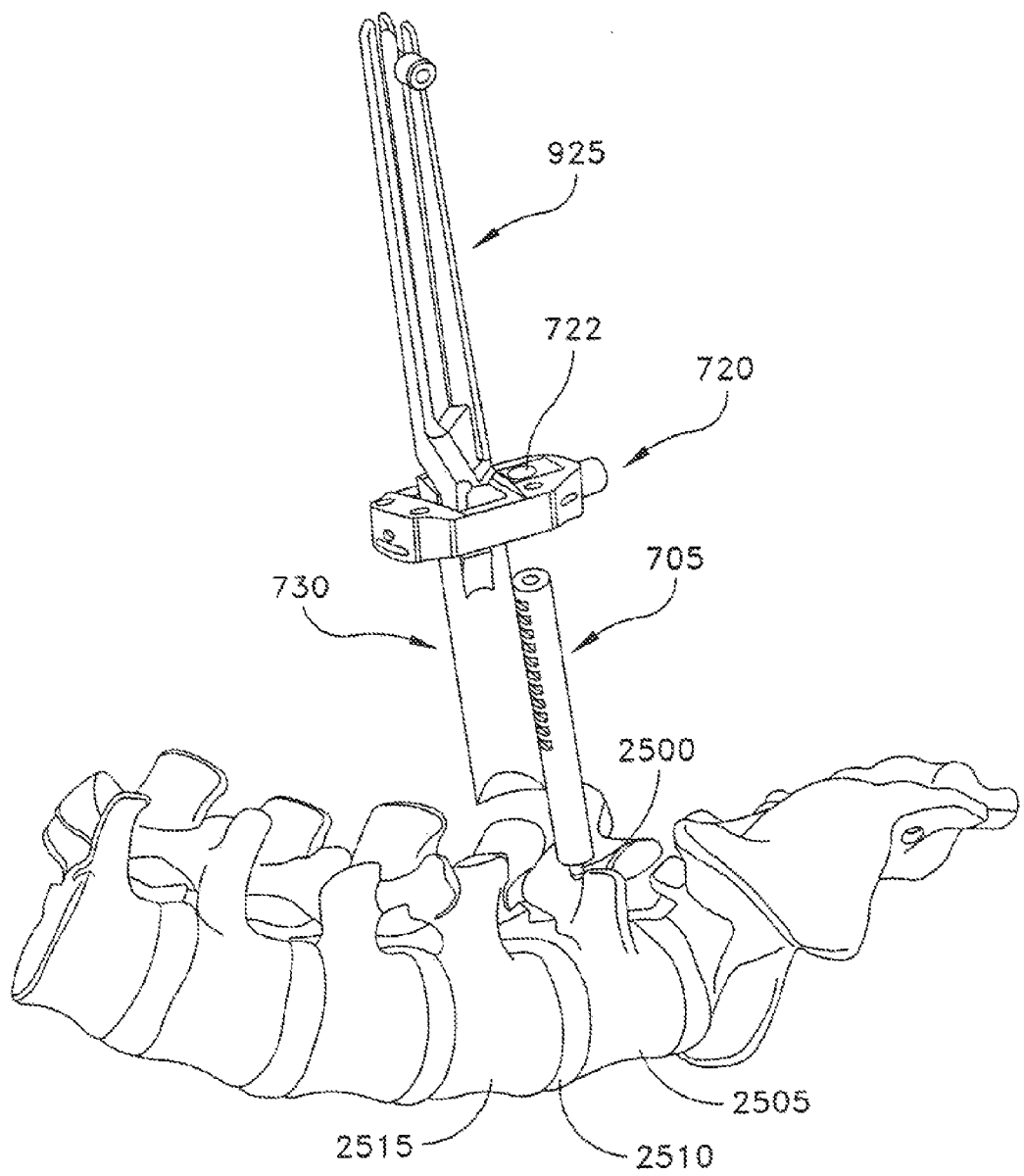
FIG. 25 is a perspective view of the retractor system of FIGS. 7 and 9 being coupled to the spine.
Figure 26:
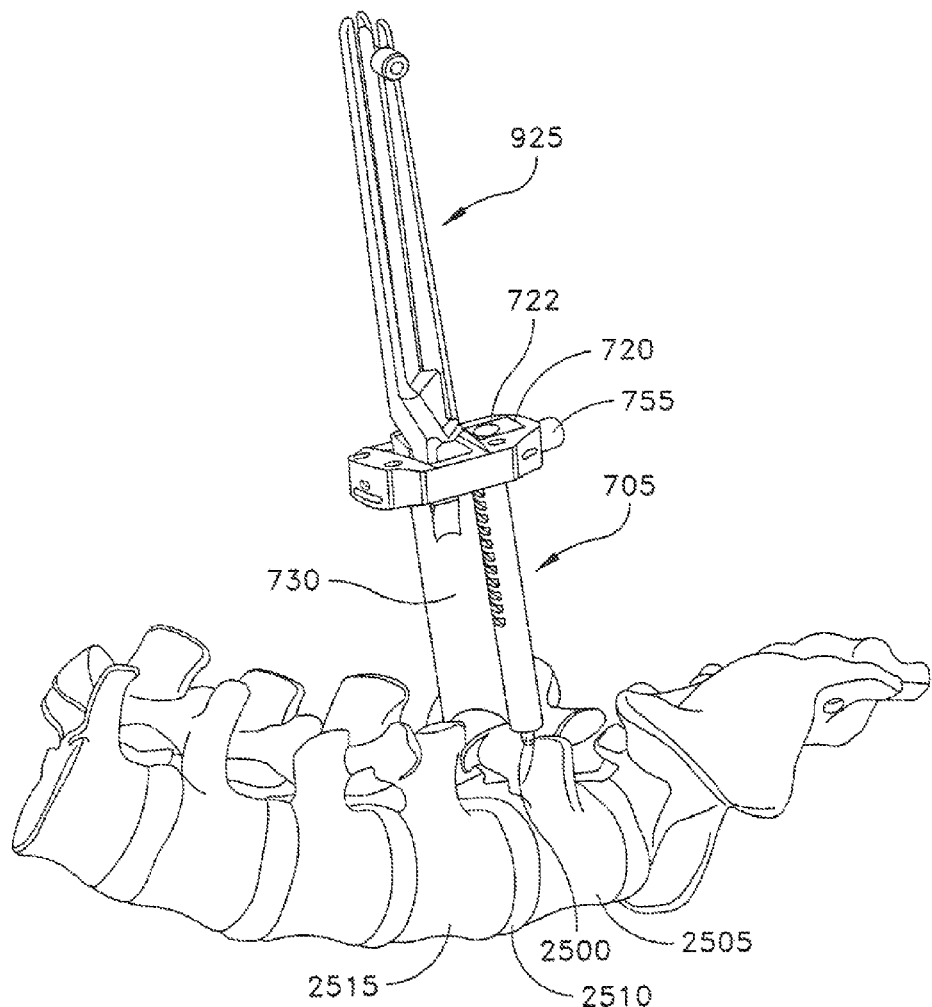
FIG. 26 is a perspective view of the retractor system of FIGS. 7 and 9 coupled to the spine and the inserter.

Inserter 925, as shown in FIG. 23, may be provided for manipulating and placing retractor body 720 along post 705. Inserter 925 may grasp retractor body 720 with blades 730 closed and centered as illustrated in FIG. 24. In some embodiments, inserter 925 includes two arms 955 rotating about a pivot 960 and having opposing distal tips 965. Distal tips 965 may engage retractor body 720, and then are held in place using a lock mechanism 970, depicted herein as a threaded nut and shaft arrangement although other locks may be used within the scope of the present disclosure. In some embodiments, distal tips 965 engage slides 725 and/or blades 730. Blades 730 may be slowly driven by retractor body 720 into the incision while confirming that post 705 slides through collar 722 of retractor body 720 as best illustrated in FIGS. 25 and 26. In some methods, one user hand engages the pedicle post 705, and the other user hand holds inserter 925 during insertion of blades 730 into the incision. For convenience and ease of understanding, FIGS. 25 and 26 have omitted certain portions of retractor system 700. While still holding inserter 925, post tightening knob 755 (also referred to as a locking nut) may be turned on retractor body 720 so as to secure retractor body 720 to post 705 at a desired location.

Figure 27:
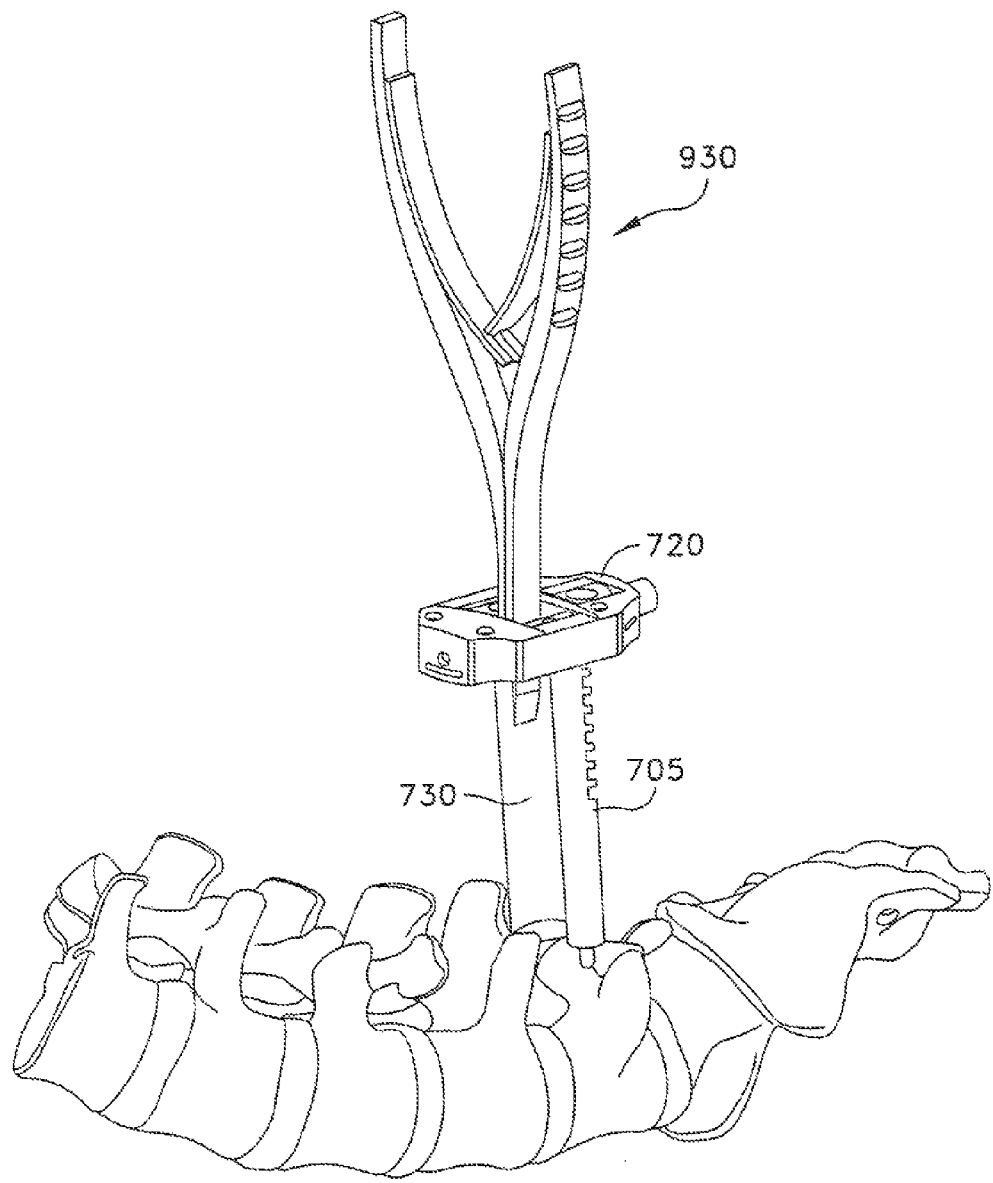
FIG. 27 is a perspective view of the retractor system of FIGS. 7 and 9 coupled to the spine in a closed configuration.
Figure 28:
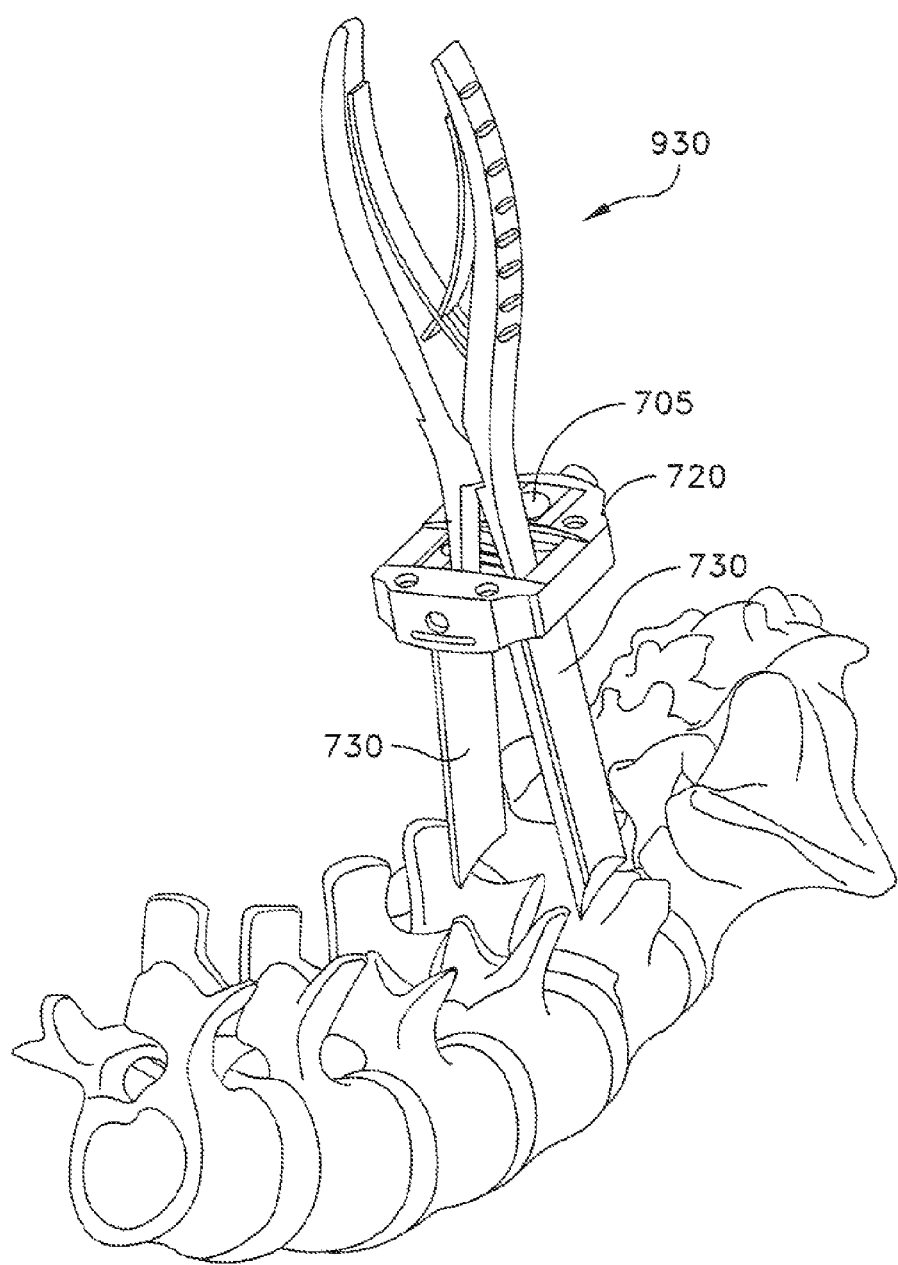
FIG. 28 is a perspective view of the retractor system of FIGS. 7 and 9 coupled to the spine in an opened configuration.

FIGS. 27 and 28 depict an embodiment for separating or opening blades 730 apart from one another with a muscle spreader 930. Other mechanisms also may be used for opening blades 730. After preferably confirming that blade tightening screw 770 is in the locked position so blades 730 are securely coupled to retractor body 720, muscle spreader 930 is used to expand blades 730. If needed or desired, a muscle splitter 935 can be used if the incision does not allow proper expansion of blades 730.

Figure 29:
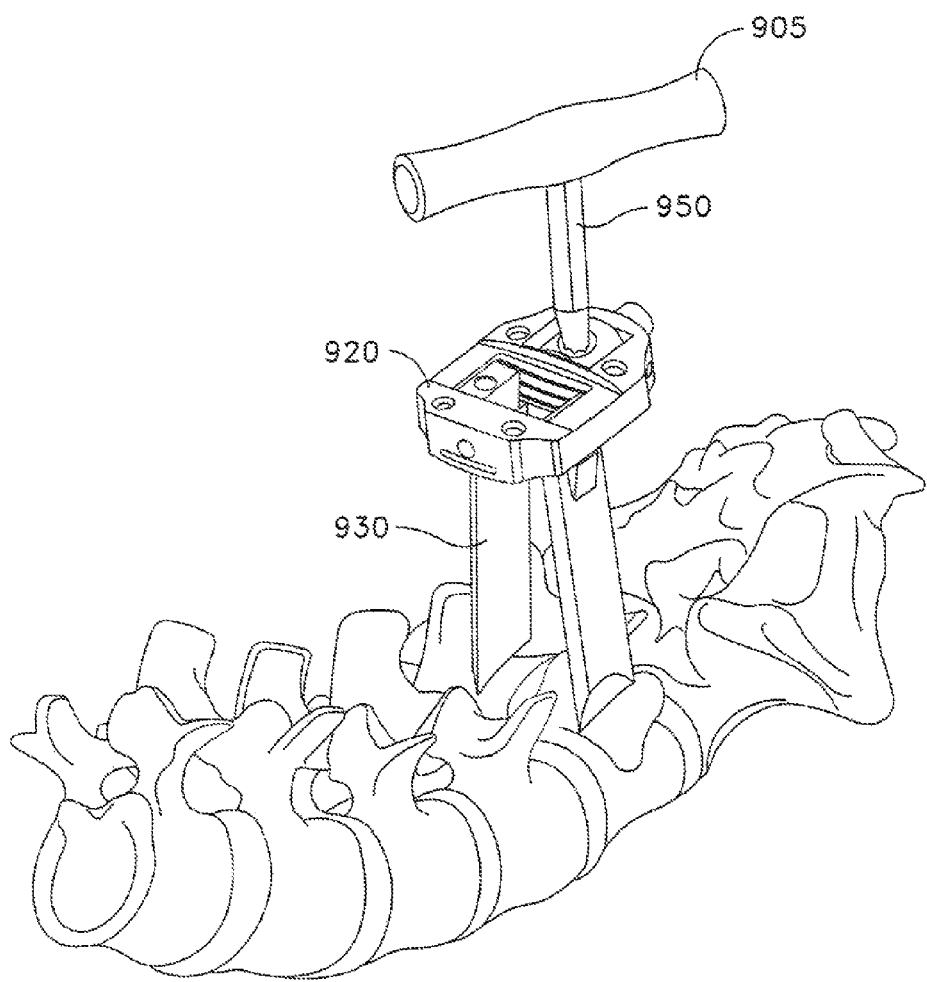
FIGS. 29-37 are perspective views at different orientations of the retractor system of FIGS. 7 and 9 coupled to the spine in the opened configuration.

With blades 730 now in position, and the angle of retractor body 720 determined, retractor body 720 is restrained and driver 905 (or another driver) is used together with T30 Torx Drive T Handle 905 (or another handle) to secure pressure core 915 in post 705 as illustrated in FIG. 29. In this manner, post 705 is secured relative to the inferior vertebrae, with pivoting and rotational movement restricted.

Figure 30:
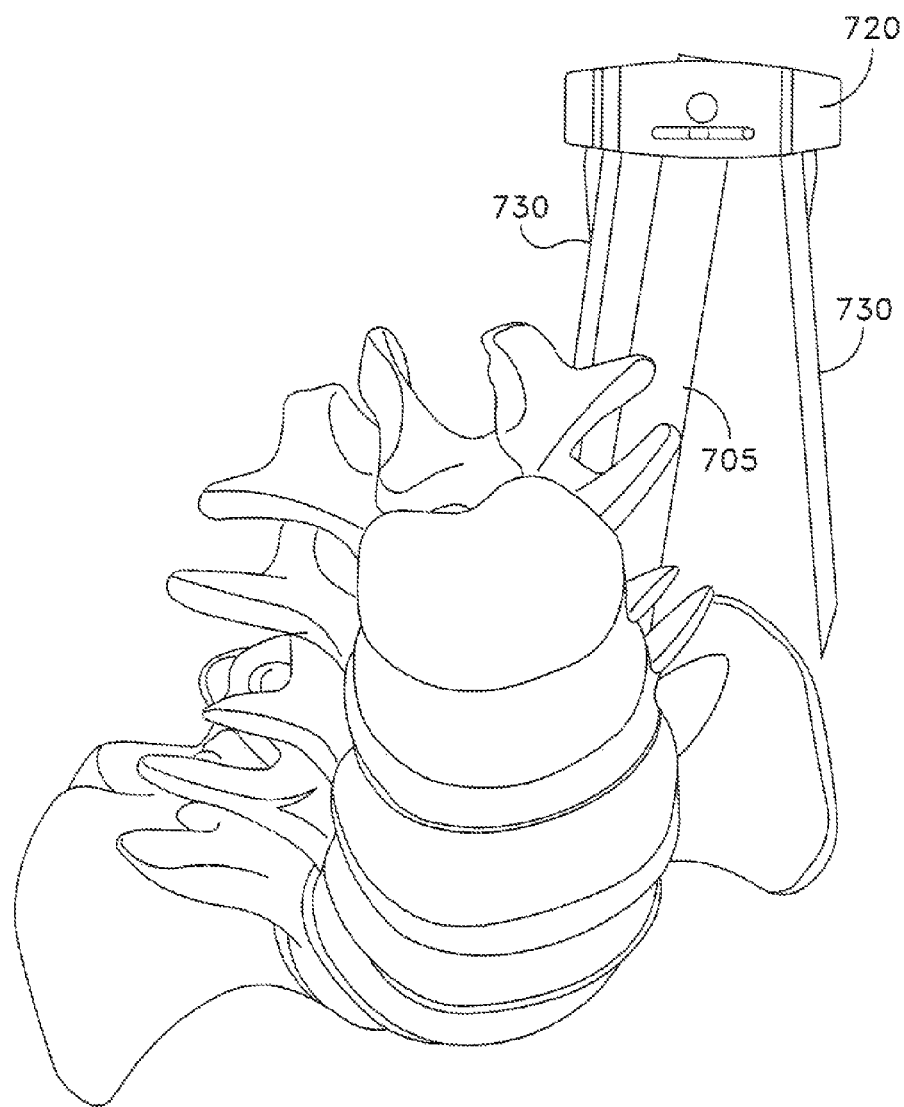
Figure 31:
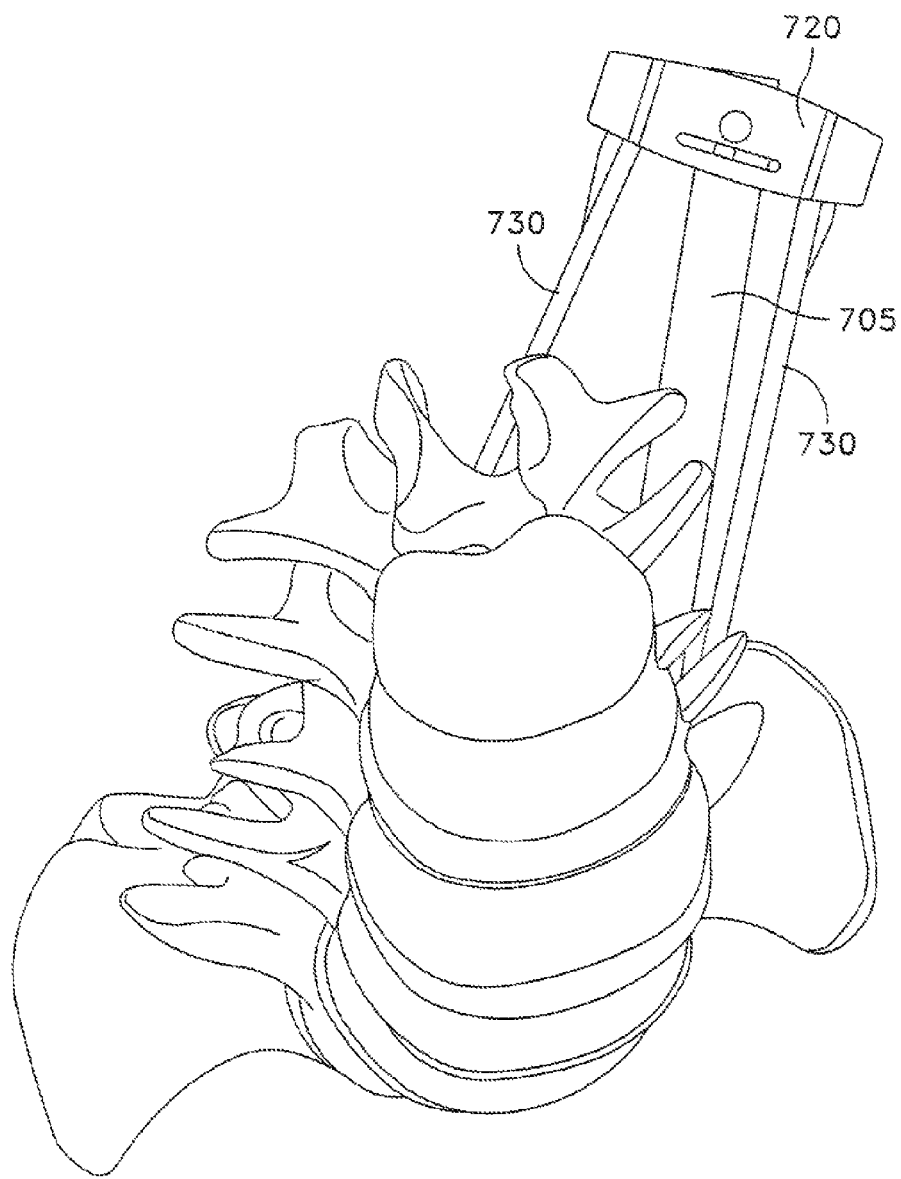
Figure 32:
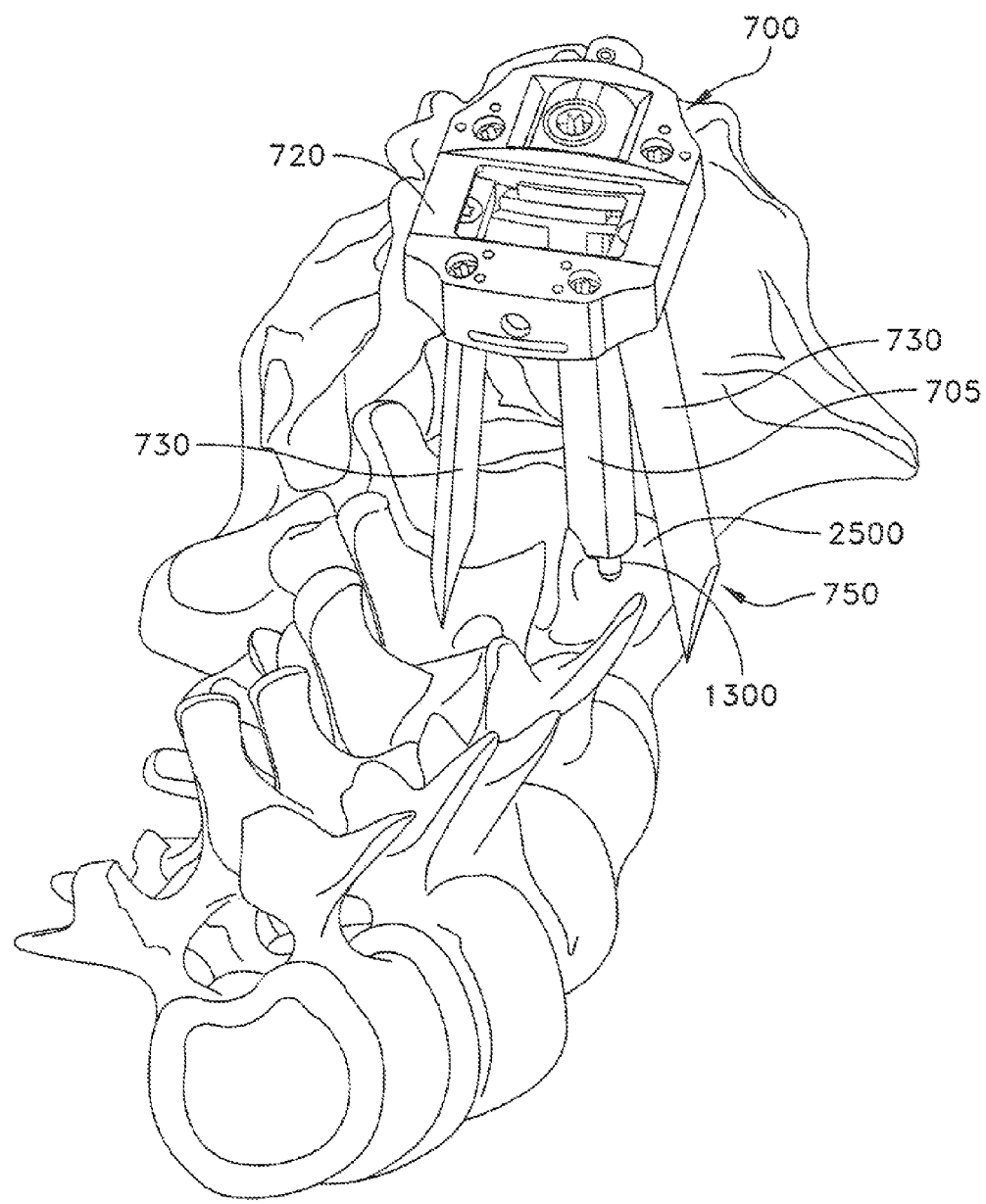
Figure 33:
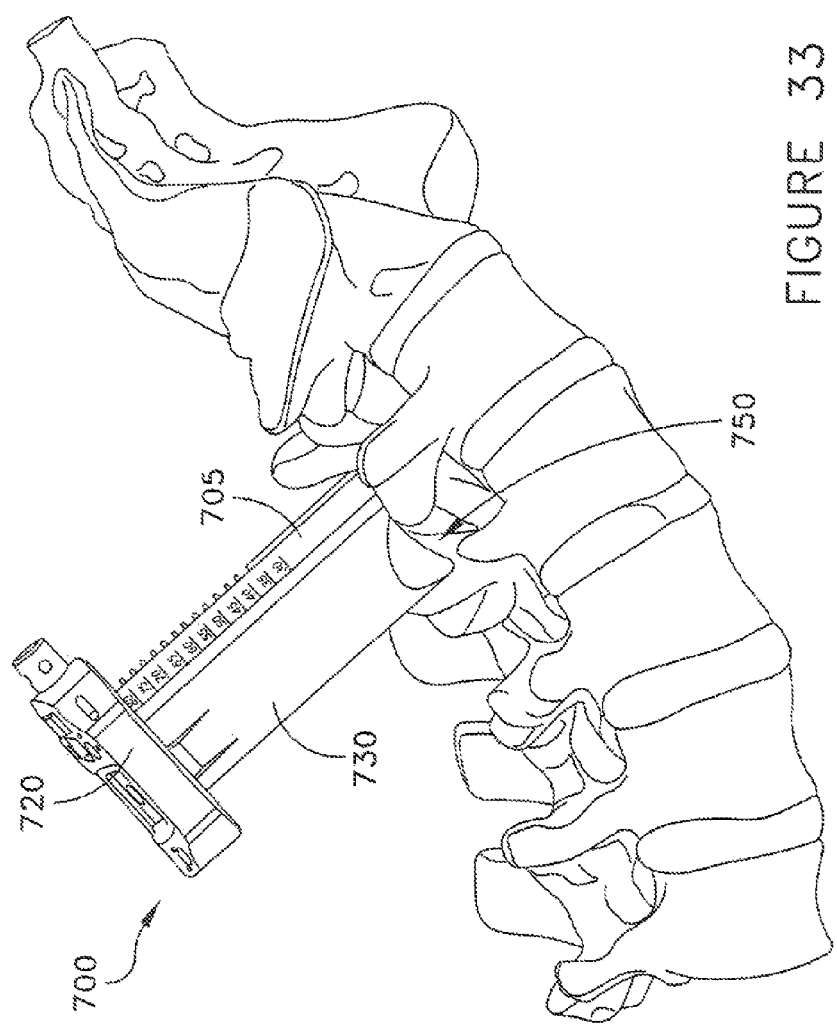
Figure 34:
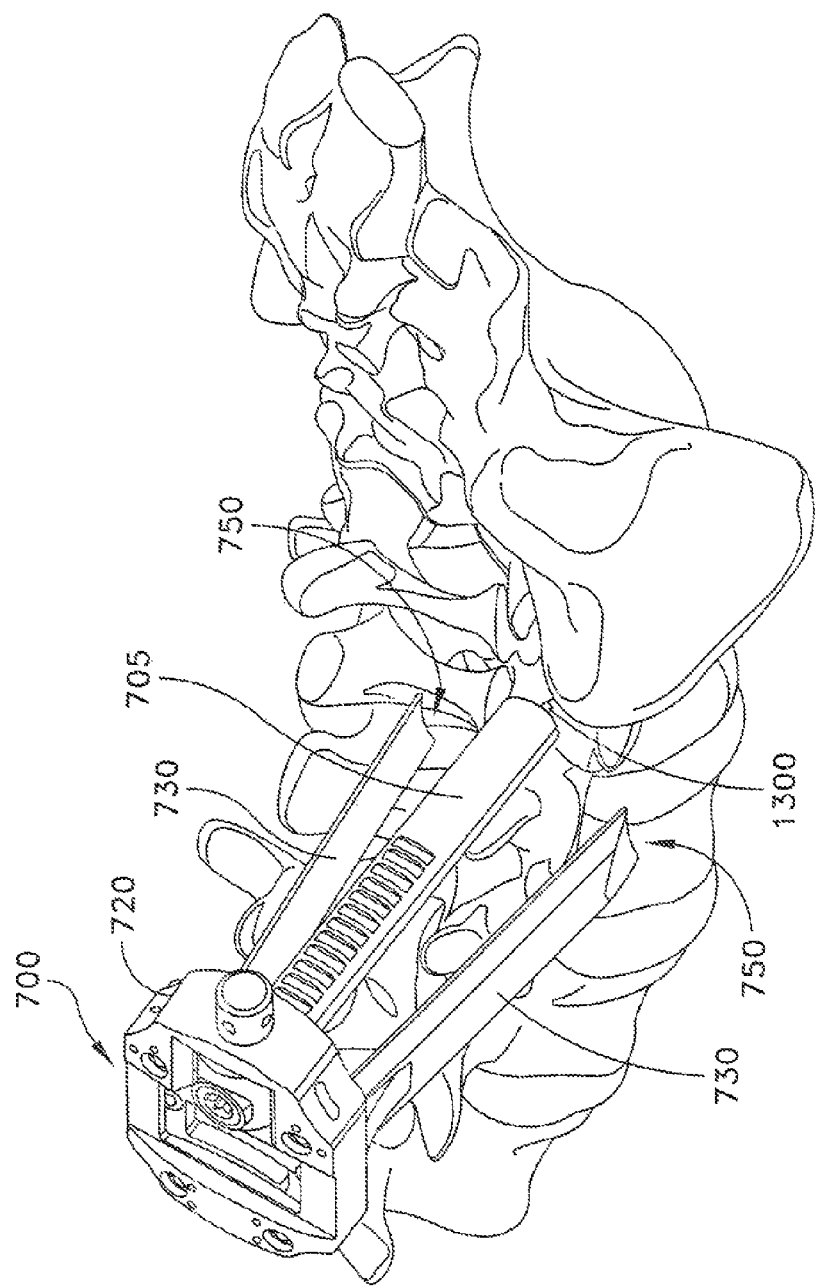
Figure 35:
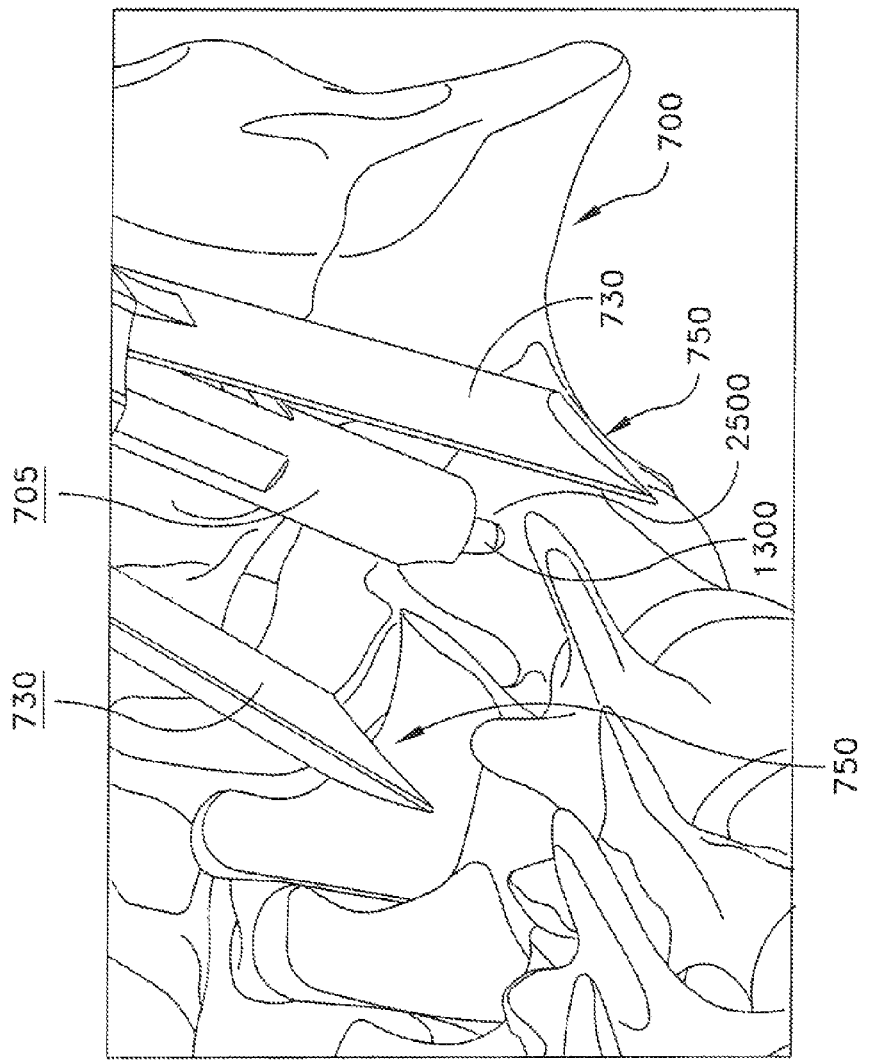
Figure 36:
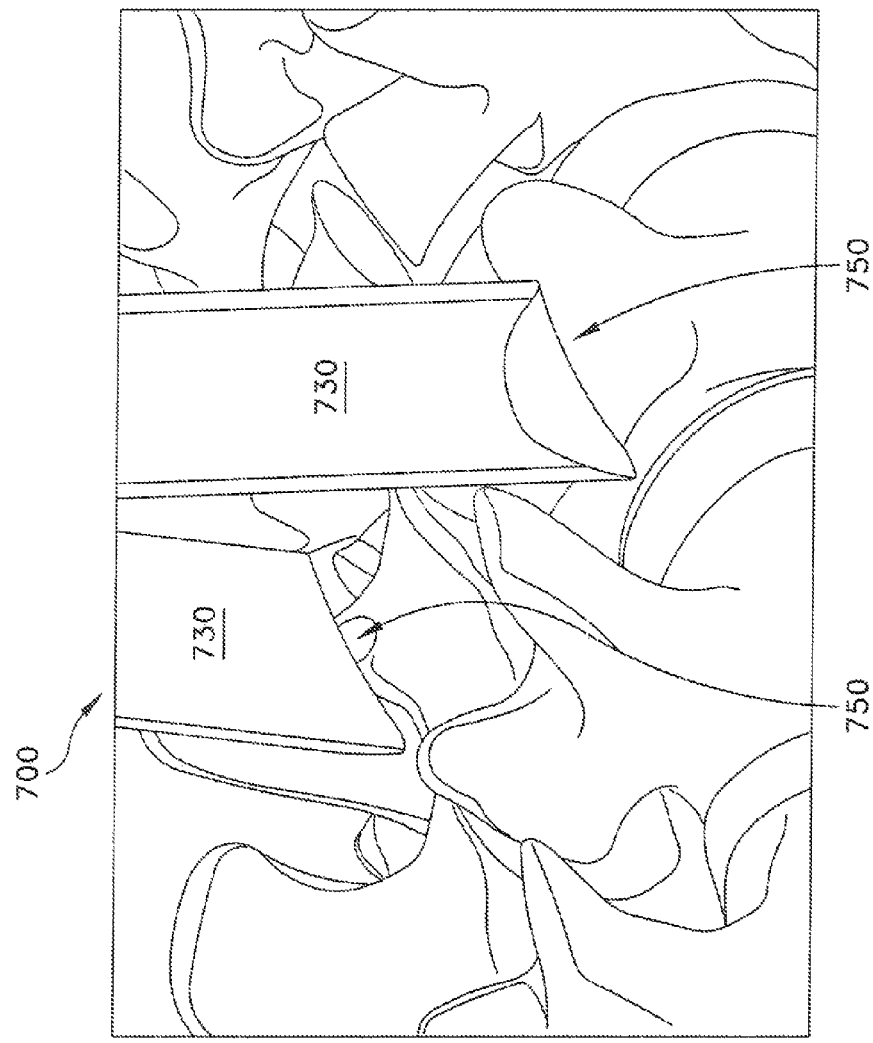
Figure 37:
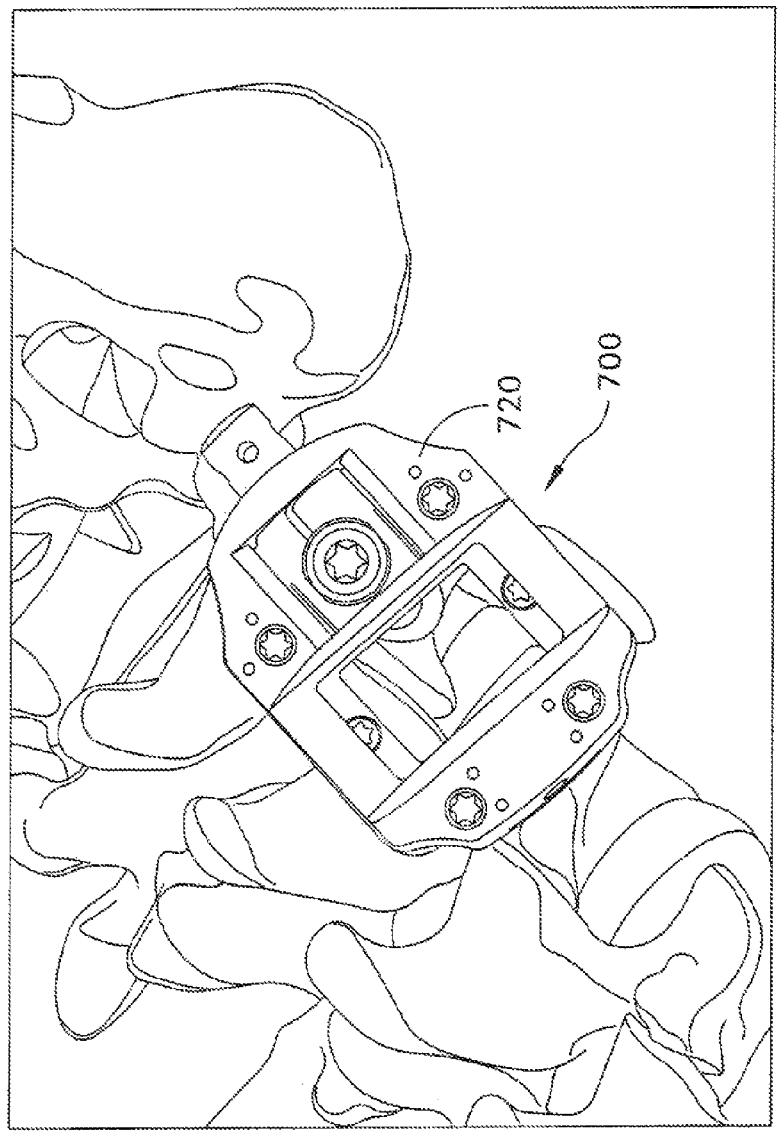

If desired, retractor body 720 may be adjusted with respect to post 705 as illustrated in FIGS. 30 and 31. For example, if the angle of retractor body 720 relative to post 705 is undesirable, roll/pitch dials 765 may be used to adjust the position of retractor body 720. Unlocking pitch/roll dials 765 releases collar 722, which allows retractor body 720 to swivel about post 705. FIGS. 30 and 31 illustrate retractor body 720 moved from a first swivel angle to a second swivel angle with respect to post 705.

FIGS. 32-37 illustrate exemplary positioning of retractor system 700 for facetectomy for the TLIF, and where the insertion of the TLIF interbody may now be safely performed. In some embodiments, geometry 750 of distal end 740 of blades 730 has a rising curve toward the superior end where post 705 is located. This geometry 750 allows the blades to closely conform to the surrounding tissue and features present at the surgical site.

Figure 38:
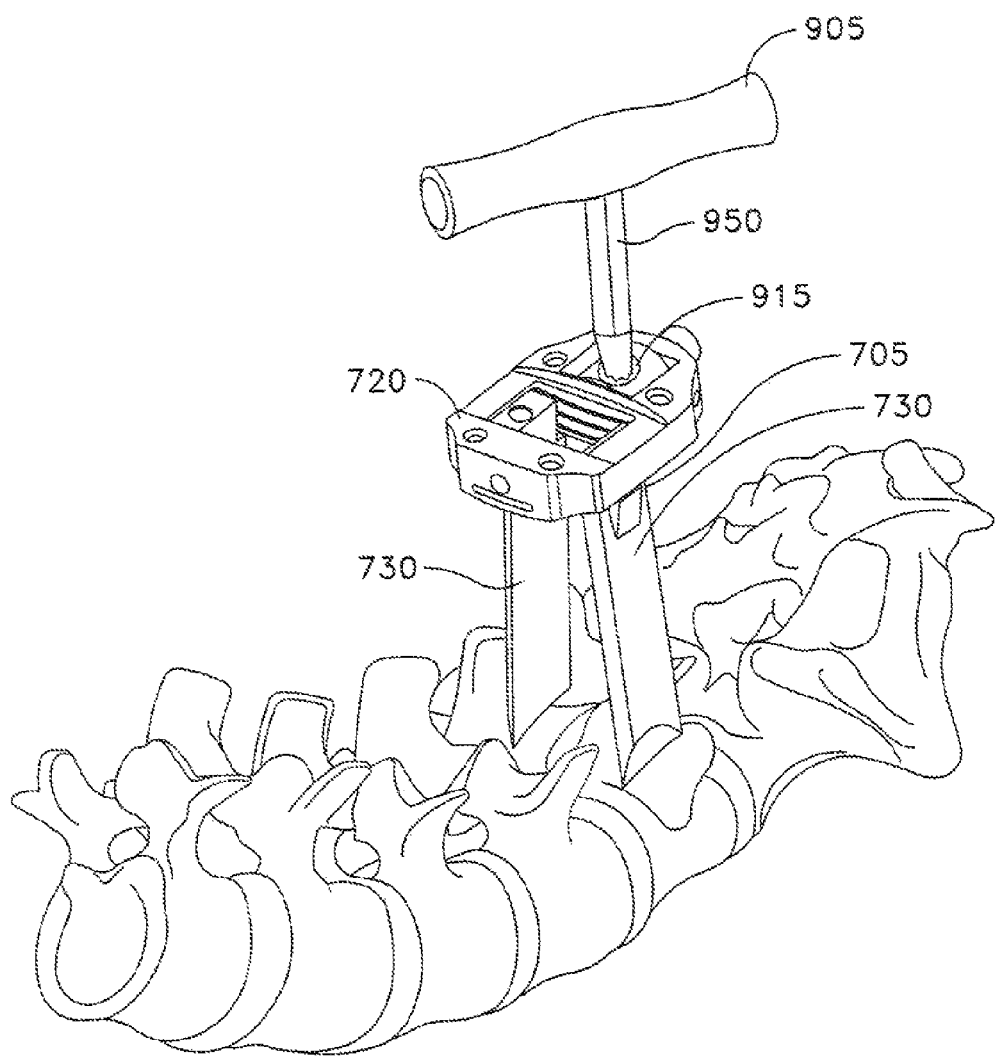
FIG. 38-40 are perspective views of removing the retractor system.

Retractor removal may include the use of driver 905, and may include T30 Torx Drive T Handle 905, to remove pressure core 915 from post 705 as illustrated in FIG. 38. Using driver 920, such as a T25 Torx Driver, blade tightening screw 770 may be released (such as by turning blade tightening screw 770 a quarter turn outwards) so as to close blades 730. Post tightening knob 755 is turned to loosen or unlock, (e.g., a counterclockwise turning) until retractor body 720 may be removed from post 705.

Figure 39:
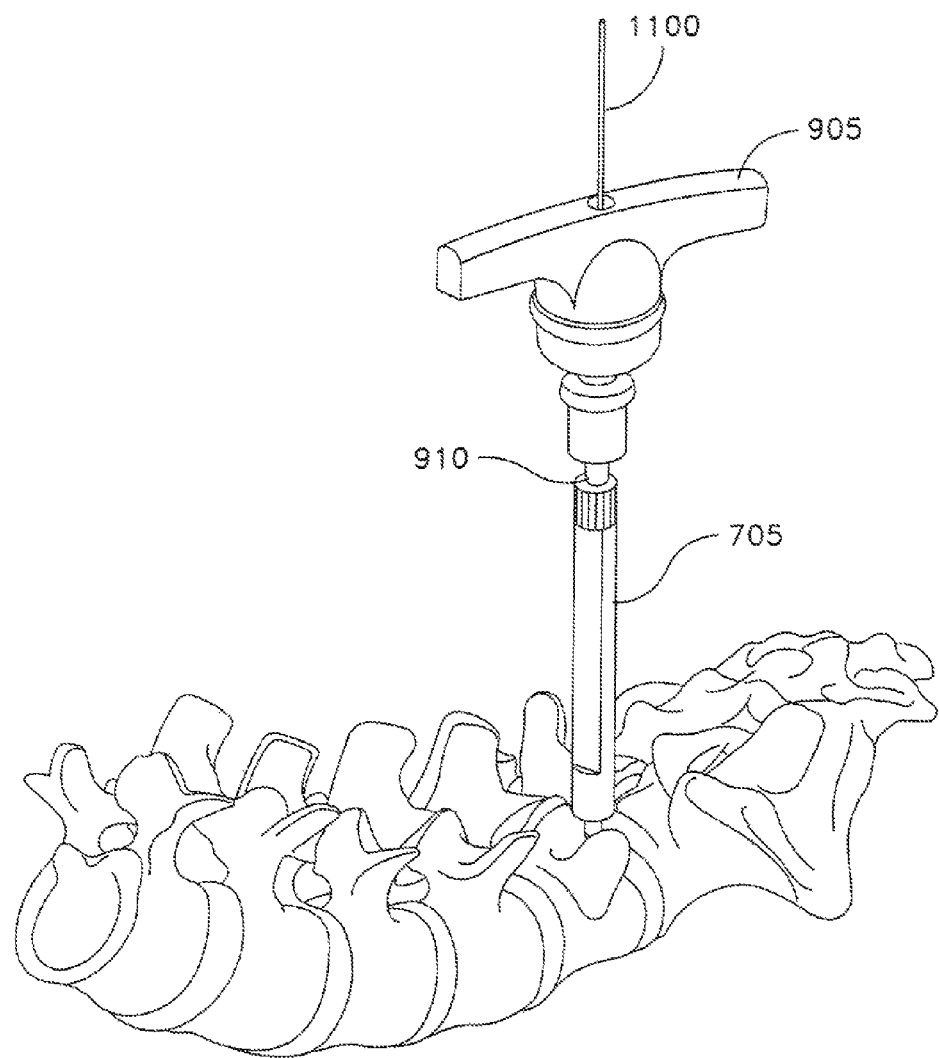

FIG. 39 illustrates a step of removal of post 705. Driver 910 may be reinserted into post 705. It should be confirmed that the hex head fully seats in the spherical head of the tap, or other secure engagement between driver 910 and anchor 1300. In some embodiments, the threaded portion of driver 910 will fully disappear once this is achieved. With driver 910 in place, a K-wire 1100 is inserted and post 705 is removed.

Figure 40:
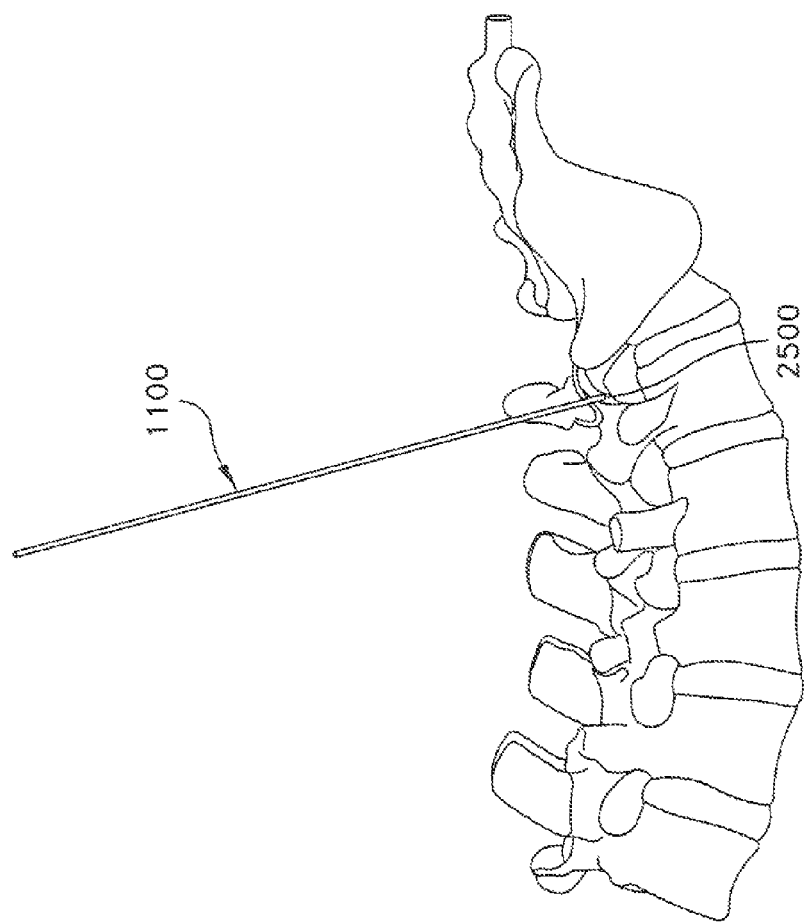

Referring now to FIG. 40, and in an embodiment, with the hole at pedicle 2500 now tapped, a screw may be inserted using typical minimally invasive surgical (MIS) techniques. It should be appreciated that it may be necessary to reinsert the dilators for such a procedure or require the hole be re-tapped to a larger size.

Figure 41:
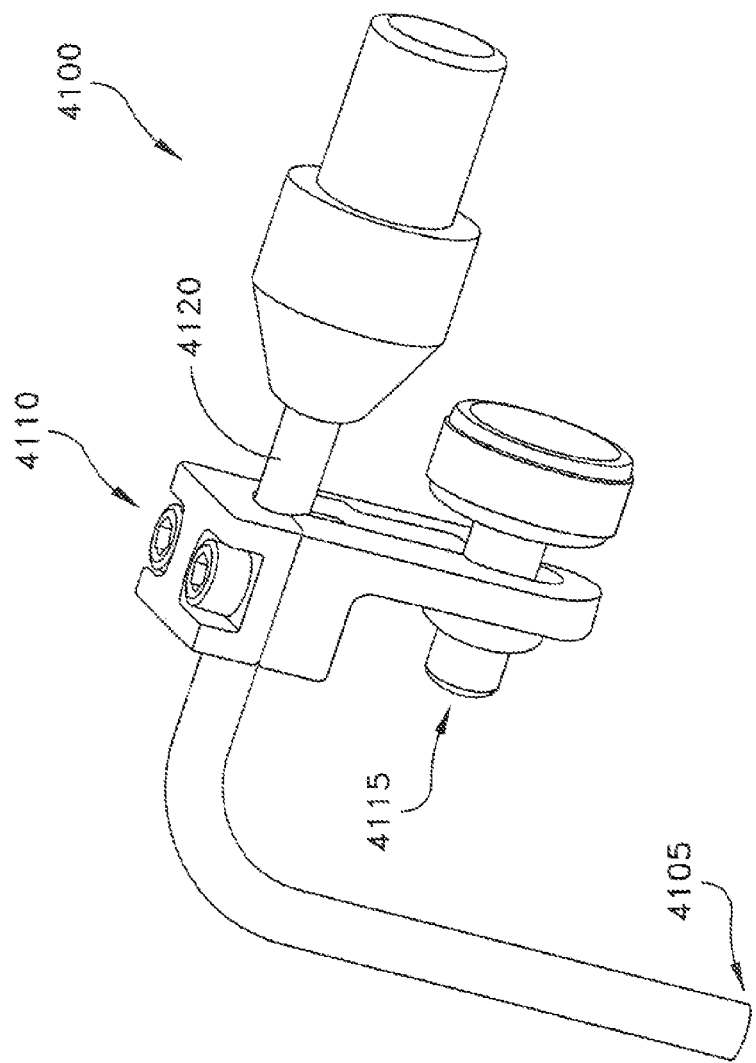
FIG. 41 is a perspective view of a light source of the retractor system of FIGS. 7 and 9.
Figure 42:
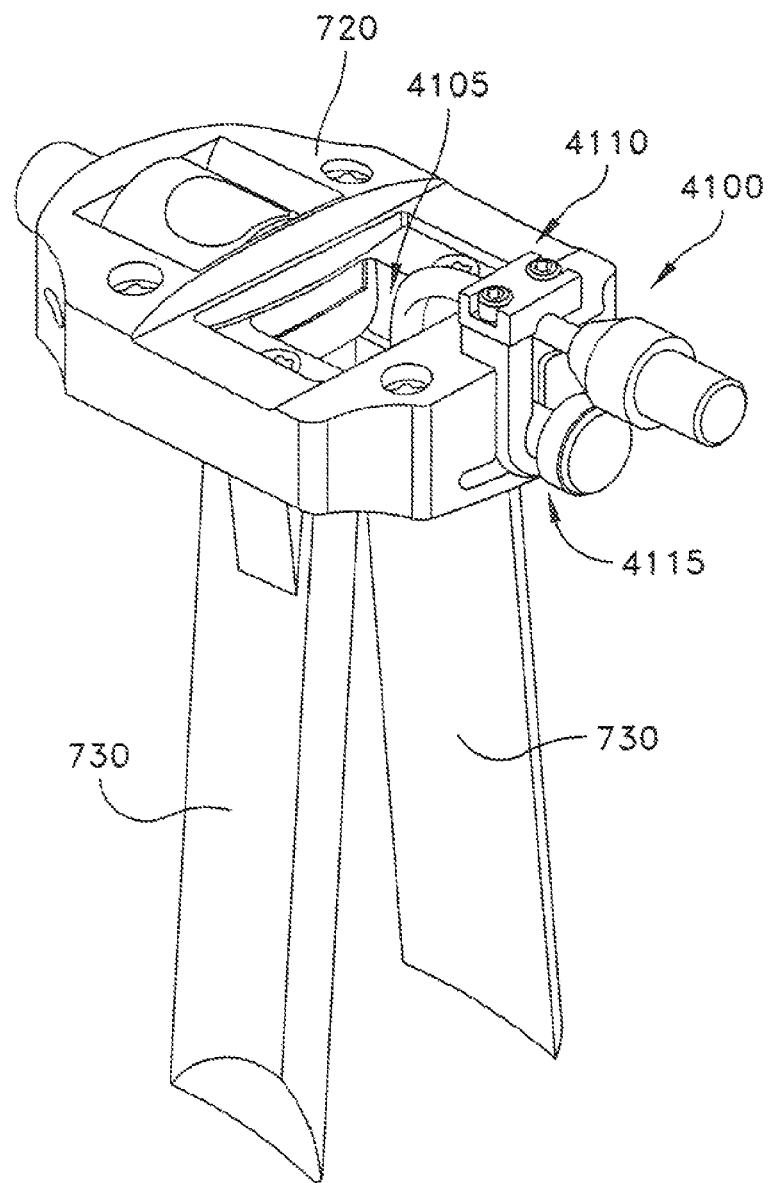
FIG. 42 is a perspective view of the light source coupled to the retractor of FIGS. 7 and 9.

Turning to FIGS. 41 and 42, a light source 4100 is depicted as an accessory light source attachment to retractor body 720. For example, a light emitter 4105 may be positioned between blades 730 using an attachment bracket 4110 with threads 4115 for insertion into retractor body 720. A shaft 4120 supports bracket 4110 and leads to light emitter 4105. With blades 730 slightly open and bracket 4110 on light source 4100 positioned appropriately on shaft 4120, light source 4100 can be moved or slid into place. A threaded hole in retractor body 720 can be aligned with the threads on bracket 4110. Light source emitter 4105 may be positioned as needed and bracket 4110 can be tightened to shaft 4120 to secure light source emitter 4105 in a desired position.

Figure 43:
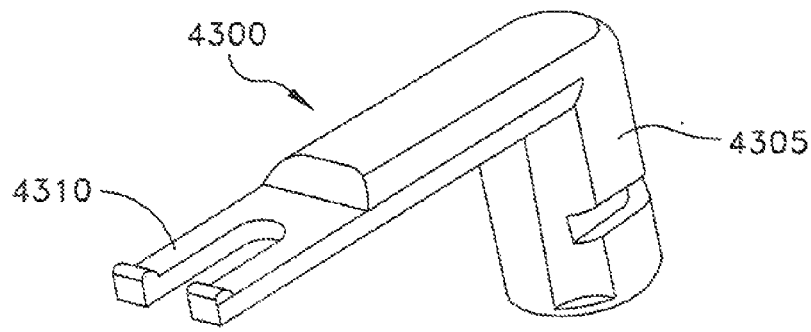
FIG. 43 is a perspective view of a snake arm of the retractor system of FIGS. 7 and 9.
Figure 44:
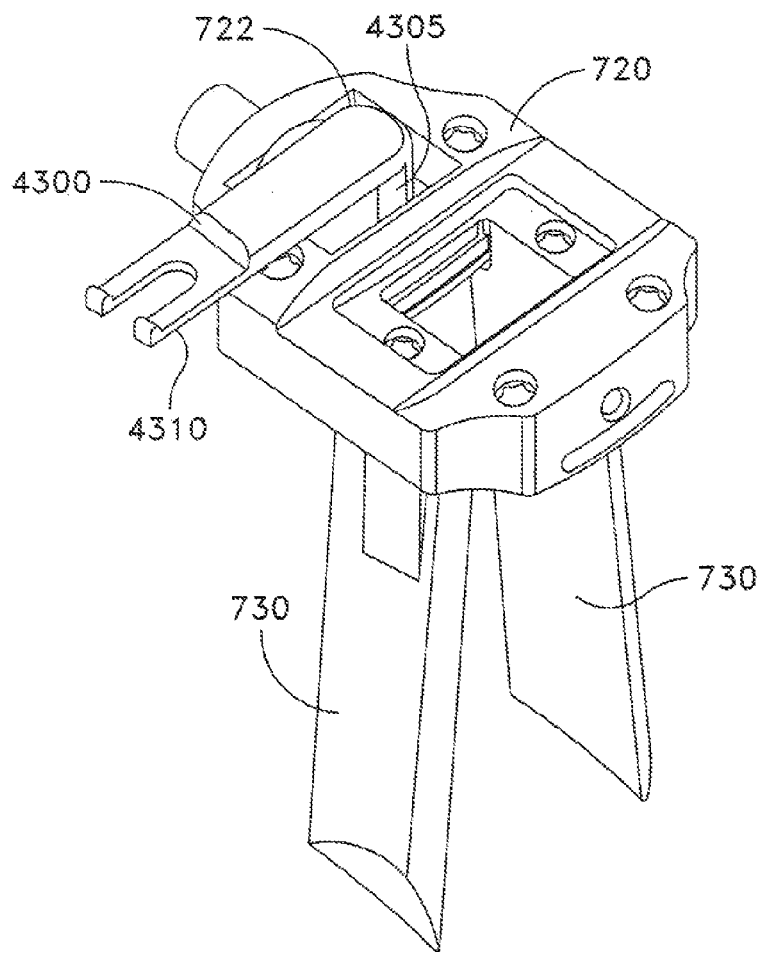
FIG. 44 is a perspective view of a snake arm adapter coupled to the retractor of FIGS. 7 and 9.

As illustrated in FIGS. 43 and 44, a snake arm connection 4300 (i.e., a manipulator connection) may include a snake arm post 4305 for connection to a collar 722 of retractor body 720 and two prongs 4310 for connection to a snakearm. Referring now to FIG. 44, snake arm connection 4300 may be placed in the position shown, or facing an opposite direction. For use without a post 705, snake arm post 4305 may be extended down through collar 722 of the retractor and secure it by turning the post tightening knob 755 of retractor body 720. A standard table snake arm can be used, and connected to the two exposed prongs 4310 of snake arm connection 4300. In this manner, a table snake arm can be used to hold retractor body 720 and blades 730 in a desired position. Alternatively a table snake arm can be used as supplemental fixation of retractor body 720 and blades 730 in addition to post 705.

We claim:

1. A retractor system to facilitate surgical access to an intervertebral disc between an inferior vertebral body and a superior vertebral body, the retractor system comprising:
   a post having a distal end and a proximal end, the distal end of the post having an anchor adapted to attach the post to a pedicle of an inferior vertebral body with respect to an intervertebral disc;
   a retractor body having a collar to adjustably attach the retractor body to the post between the distal end and the proximal end of the post, a pair of slides adjustably coupled to the retractor body, the slides configured for selective adjustment with respect to one another between a substantially closed position and an opened position with the slides further apart than the substantially closed position, and a pair of blades mounted to the slides, each one of the blades having a proximal end and a distal end, a distance between the proximal end and the distal end of each one of the blades configured for displacing tissue for access to an intervertebral disc, an attachment portion adjacent the proximal end of each one of the blades for attaching one of the slides thereto, and a geometry of the distal end of each one of the blades for conforming to anatomy surrounding the pedicle; and a pitch/roll adjustment mechanism in the retractor body to control the orientation of the retractor body relative to the post.

2. The retractor system of claim 1, further comprising a post tightening knob to interoperate with the collar by adjusting a position of a protrusion within the collar, wherein the protrusion provides a selective engagement to hold the post within the collar.

3. The retractor system of claim 1, further comprising a blade tightening screw in communication with each one of the slides so as to selectively secure and release the blades from the retractor body.

4. The retractor system of claim 3, further comprising a threaded adjustment for the blade tightening screw.

5. The retractor system of claim 1, further comprising a slide lock in communication with at least one of the slides to selectively lock and release the slides with respect to the retractor body.

6. The retractor system of claim 5, further comprising a ratchet adjustment for the slide lock.

7. The retractor system of claim 1, further comprising a dial adjustment for the pitch/roll adjustment of the retractor body.

8. The retractor system of claim 1, further comprising a second post having a second anchor adapted to attach the second post to a pedicle of a superior vertebral body.

9. The retractor system of claim 1, wherein the retractor body is adjustably attached to the second post.

10. A retractor system to facilitate surgical access to an intervertebral disc between an inferior vertebral body and a superior vertebral body, the retractor system comprising:
  a retractor body;
  a means adapted for attaching the retractor body to a vertebral body, wherein the retractor body comprises a means for adjusting the orientation of the retractor body to the means for attaching, a pair of slides adjustably coupled to the retractor body, the slides configured for selective adjustment with respect to one another between a substantially closed position and an opened position with the slides further apart than the substantially closed position, and a pair of blades mounted to the slides, each one of the blades having a proximal end and a distal end, a distance between the proximal end and the distal end of each one of the blades configured for displacing tissue for access to an intervertebral disc, an attachment portion adjacent the proximal end of each one of the blades for attaching one of the slides thereto, and a geometry of the distal end of each one of the blades for conforming to anatomy surrounding the pedicle; and
  a pitch/roll adjustment mechanism in the retractor body to control the orientation of the retractor body relative to the means adapted for attaching the retractor body to the vertebral body within the retractor body.

11. The retractor system of claim 10, wherein the means adapted for attaching the retractor body to the vertebral body comprises a post having a distal end and a proximal end, the distal end of the post having an anchor adapted to attach the post to a pedicle of an inferior vertebral body with respect to an intervertebral disc.

12. The retractor system of claim 10, wherein the means adapted for attaching the retractor body to the vertebral body comprises a post having a distal end and a proximal end, the distal end of the post having an anchor adapted to attach the post to a pedicle of a superior vertebral body with respect to an intervertebral disc.

13. The retractor system of claim 10, wherein the means adapted for attaching the retractor body to the vertebral body comprises first and second posts having first and second anchors, respectively, with the first anchor adapted to attach the first post to a pedicle of an inferior vertebral body with respect to an intervertebral disc space, and the second anchor adapted to attach the second post to a pedicle of a superior vertebral body with respect to the intervertebral disc space.

14. The retractor system of claim 13, further comprising a shroud coupled between the first and second posts, the shroud adapted to provide access to the intervertebral disc space.

15. The retractor system of claim 14, wherein the shroud is disposed around the pair of blades.

16. The retractor system of claim 10, wherein the means for adjusting the orientation of the retractor body to the means for attaching includes a collar to adjustably attach the retractor body to the means adapted for attaching the retractor body to the vertebral body.

17. A retractor system to facilitate surgical access to a spinal segment, the retractor system comprising:
  a retractor body having an opening disposed therethrough and first and second slides adjustably coupled to the retractor body;
  first and second retractor blades coupled to the first and second slides, respectively, and movable relative to the retractor body;
  an elongate member having a distal end and a proximal end, the elongate member distal end having an anchor adapted to attach the elongate member to a vertebral body, and wherein the elongate member distal end is rotatable and pivotable relative to the elongate member proximal end when in an unlocked configuration;
  a locking member adapted to secure the elongate member distal end in a locked configuration relative to the elongate member proximal end; and
  a pitch/roll adjustment mechanism in the retractor body to control the orientation of the retractor body relative to the elongate member.

18. The retractor system of claim 17, wherein the locking member comprises a core member adapted to be received within a lumen disposed in the elongate member, the core member having a distal end which engages the elongate member distal end to restrict rotational and pivotable motion between the elongate member distal and proximal ends.

* * * * *